United States Patent [19]
Haase et al.

[11] Patent Number: 5,813,303
[45] Date of Patent: Sep. 29, 1998

[54] APPARATUS FOR CUTTING A SURGICAL SUTURE AT TWO LOCATIONS

[75] Inventors: Bernd Haase, Berkeley Heights, N.J.; John J. Price, Gainesville, Ga.; Kenneth J. Smith, Somerville, N.J.

[73] Assignee: Ethicon, Inc., Somerville, N.J.

[21] Appl. No.: 644,871

[22] Filed: May 10, 1996

[51] Int. Cl.$^6$ ................................................. B26D 1/00
[52] U.S. Cl. ......................... 83/170; 83/171; 83/206; 83/277; 83/649
[58] Field of Search ........................... 83/649, 170, 171, 83/206, 277, 83, 85, 913, 950

[56] References Cited

U.S. PATENT DOCUMENTS

| | | | |
|---|---|---|---|
| 284,496 | 9/1883 | Seymour | 83/636 |
| 1,492,821 | 5/1924 | Weinbach | 219/535 X |
| 1,651,834 | 12/1927 | Novick | 83/623 X |
| 1,665,216 | 4/1928 | Morton et al. | 219/50 X |
| 2,173,789 | 9/1939 | Nikles et al. | 83/913 X |
| 2,236,833 | 4/1941 | Pell et al. | 83/636 X |
| 2,803,109 | 8/1957 | Stoddard | 219/388 X |
| 2,997,905 | 8/1961 | Larson | 83/171 |
| 3,165,958 | 1/1965 | Anderson et al. | 83/170 |
| 3,317,924 | 5/1967 | Le Veen et al. | 156/174 X |
| 3,376,698 | 4/1968 | Whittaker | 57/282 |
| 3,388,030 | 6/1968 | Estes et al. | 156/180 X |
| 3,449,549 | 6/1969 | Isobe et al. | 219/388 |
| 3,472,108 | 10/1969 | Vandersip | 83/950 X |
| 3,479,670 | 11/1969 | Medell | 156/425 X |
| 3,564,958 | 2/1971 | Richter | 83/100 |
| 3,642,010 | 2/1972 | Kuris | 132/201 |
| 3,736,646 | 6/1973 | Schmitt et al. | 156/180 X |
| 3,807,270 | 4/1974 | Wirz | 83/639.7 X |
| 3,835,912 | 9/1974 | Kristensen et al. | 228/903 X |
| 3,890,975 | 6/1975 | McGregor | 163/1 X |
| 3,943,933 | 3/1976 | Gertzman | 204/157.63 X |
| 3,949,756 | 4/1976 | Ace | 163/1 X |
| 3,980,177 | 9/1976 | McGregor | 206/63.3 |
| 3,981,307 | 9/1976 | Borysko | 163/1 X |
| 4,014,648 | 3/1977 | Walsh et al. | 83/913 X |
| 4,017,012 | 4/1977 | Brock | 83/171 X |
| 4,041,814 | 8/1977 | High | 83/950 X |
| 4,048,833 | 9/1977 | Lorenz et al. | 83/277 X |
| 4,173,311 | 11/1979 | Lucke | 83/909 X |
| 4,358,976 | 11/1982 | Alviti | 83/277 X |
| 4,460,820 | 7/1984 | Matsumoto et al. | 219/385 |
| 4,470,941 | 9/1984 | Kurtz | 264/171.23 X |
| 4,510,934 | 4/1985 | Batra | 606/231 |
| 4,605,115 | 8/1986 | Genans | 83/277 X |
| 4,669,474 | 6/1987 | Barrows | 606/152 |
| 4,694,718 | 9/1987 | Kinsley | 83/385 X |
| 4,716,801 | 1/1988 | Spaller, Jr. | 83/67 X |
| 4,806,737 | 2/1989 | Coates | 219/390 |
| 4,832,025 | 5/1989 | Coates | 606/224 |
| 4,922,904 | 5/1990 | Uetake et al. | 606/226 |
| 5,226,336 | 7/1993 | Coates | 83/909 X |
| 5,349,890 | 9/1994 | Butkus et al. | 83/171 |
| 5,452,636 | 9/1995 | Rattan | 83/950 X |

FOREIGN PATENT DOCUMENTS

| | | |
|---|---|---|
| 0950830 | 8/1982 | U.S.S.R. |
| 0568675 | 4/1945 | United Kingdom. |
| 0950339 | 2/1964 | United Kingdom. |
| 0996908 | 6/1965 | United Kingdom. |

*Primary Examiner*—Maurina T. Rachuba
*Attorney, Agent, or Firm*—Hal Brent Woodrow

[57] ABSTRACT

An apparatus and method for cutting a surgical suture at a first and second different location along its length. The apparatus having a first and a second cutting die with channels for receiving at least a portion of the cross-section of the surgical suture at each location. Each of the first and second cutting dies respectively is provided with an opposing cutting die to further restraint the suture. A blade is also provided at each cutting location for cutting the suture at a point adjacent to the respective cutting dies when the suture is restrained between the sets of dies.

12 Claims, 23 Drawing Sheets

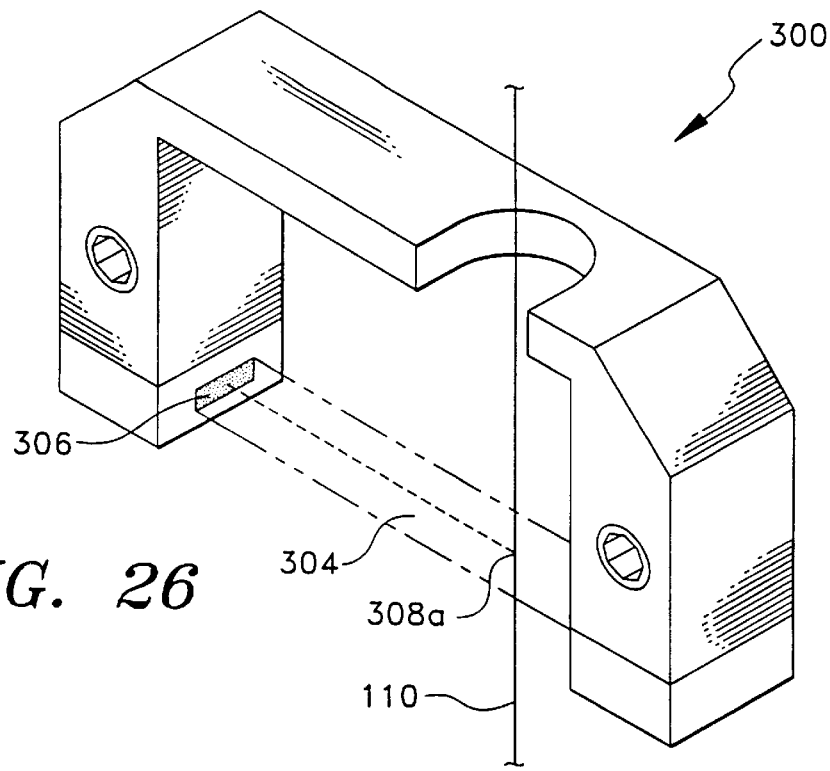
FIG. 26
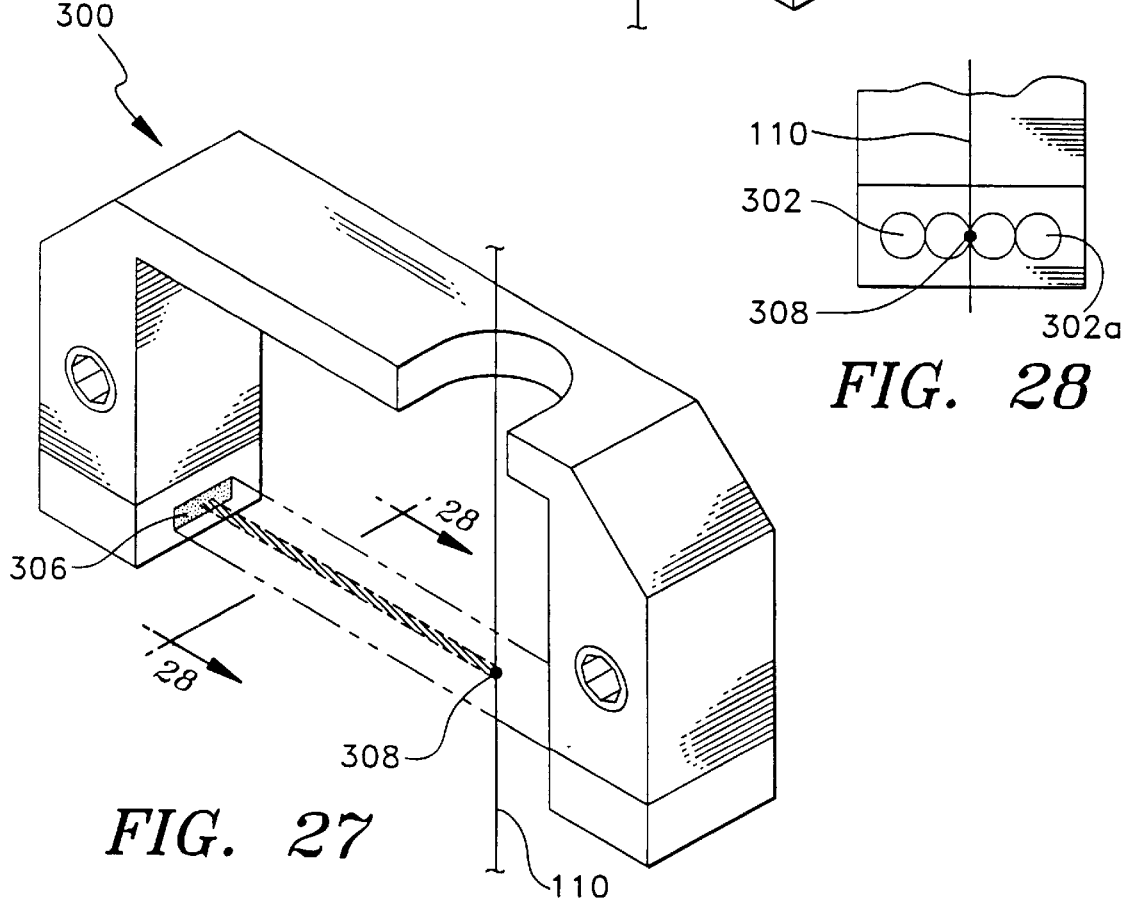
FIG. 28
FIG. 27

APPARATUS FOR CUTTING A SURGICAL SUTURE AT TWO LOCATIONS

FIELD OF THE INVENTION

The present invention is directed to systems for processing strings and yarns. More particularly, the present invention is directed to automated systems for thermally forming and cutting surgical sutures.

BACKGROUND OF THE INVENTION

Various automated systems for forming and cutting surgical suture tips exist or are known in the art. In one such machine, means for simultaneously advancing in parallel at least six separate strands of suture material, and six independent tensioners for maintaining respective parallel portions of each of the six strands at a preset tension are provided. Once a predetermined length of suture material had been advanced by the advancing means, a horizontal heater bar (positioned perpendicular to the six suture strands) is actuated by an electronically controlled solenoid which moves a planar heater bar into contact with one side of the suture strands for a predetermined dwell time. Once the predetermined dwell time has elapsed, the solenoid retracts the heater bar to its original position, and the heat exposed (or heat-stiffened) section of suture material is advanced to a cutting station. At the cutting station, the heat-stiffened section of suture material is cut at its midpoint, thereby producing a suture with two stiffened ends. Other mechanisms for forming and cutting surgical suture tips are shown in U.S. Pat. Nos. 4,832,025, 4,806,737 and 5,226,336 to Coates. The system described in the Coates patents uses convective or non-contact heating to form suture tips.

Known systems for forming and cutting surgical suture tips suffer from two primary drawbacks. First, such systems typically produce a suture tip which lacks a substantially uniform cross-section. Second, such systems typically cut the suture tip in an imprecise manner, thereby leaving a cut end which may be irregular or distorted in shape. From a manufacturing standpoint, suture tips having non-uniform cross-sections and/or irregular or distorted cut ends are undesirable because, among other things, such sutures are difficult to insert into needles.

It is therefore an object of the present invention to provide a surgical suture having a tip with a substantially uniform cross-section and a precisely cut end which may be easily inserted into a needle.

It is a further object of the present invention to an automated system and method for manufacturing surgical sutures having tips with substantially uniform cross-sections.

It is a still further object of the present invention to provide an automated system and method for making surgical sutures with tips having precisely cut ends.

These and other objects and advantages of the invention will become more fully apparent from the description and claims which follow or may be learned by the practice of the invention.

SUMMARY OF THE INVENTION

The present invention is directed to an apparatus for cutting a surgical suture at first and second different locations along its length, the surgical suture having a cross-section that is perpendicular to its length. A first cutting die having a first face with a first channel therein is provided for receiving at least a portion of the cross-section of the surgical suture at the first location along the length of the surgical suture. A second cutting die having a second face with a second channel therein is provided for receiving at least a portion of the cross-section of the surgical suture at the second location along the length of the surgical suture. A third cutting die having a third face and a fourth cutting die having a fourth face are also provided. A first cutting blade is provided for cutting the surgical suture at a point adjacent to the first location when the first face of the first cutting die is positioned against the third face of the third cutting die. Finally, a second cutting blade is provided for cutting the surgical suture at a point adjacent to the second location when the second face of the second cutting die is positioned against the fourth face of the fourth cutting die and the cross-section of the surgical suture at the first location along the length of the surgical suture is at least partially positioned in the first channel.

In accordance with a still further aspect, the present invention is directed to a method for cutting a surgical suture at first and second different locations along its length, the surgical suture having a cross-section that is perpendicular to its length. The length of surgical suture is positioned between a first channel in a first face of a first cutting die and a third face of a third cutting die, and between a second channel in a second face of a second cutting die and a fourth face of a fourth cutting die. After the positioning step, at least a portion of the cross-section of the surgical suture at the first location along the length of the surgical suture is received into the first channel and the first and third faces of the first and third cutting dies, respectively, are moved against each other. In addition, after the positioning step, at least a portion of the cross-section of the surgical suture at the second location along the length of the surgical suture is received into the second channel and the second and fourth faces of the second and fourth cutting dies, respectively, are moved against each other. Next, a first cutting blade is moved across a point adjacent to the first location when the first face of the first cutting die is positioned against the third face of the third cutting die. While the cross-section of the surgical suture at the first location along the length of the surgical suture is at least partially positioned in the first channel and the second face of the second cutting die is positioned against the fourth face of the fourth cutting die, a second cutting blade is moved across a point adjacent to the second location.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

FIG. 26 is an isometric view of an optical detection system for detecting knots in surgical suture material passing through the system, in accordance with a preferred embodiment of the present invention.

FIG. 27 is a further isometric view showing a knot positioned between the optical source and the optical detector of the knot detection system of FIG. 26, in accordance with a preferred embodiment of the present invention.

FIG. 28 is a cross-sectional view of FIG. 27, showing a knot positioned between the optical source and the optical detector of the knot detection system of FIG. 26, in accordance with a preferred embodiment of the present invention.

DETAILED DESCRIPTION OF THE INVENTION

Overall System Operation

Figure 1:
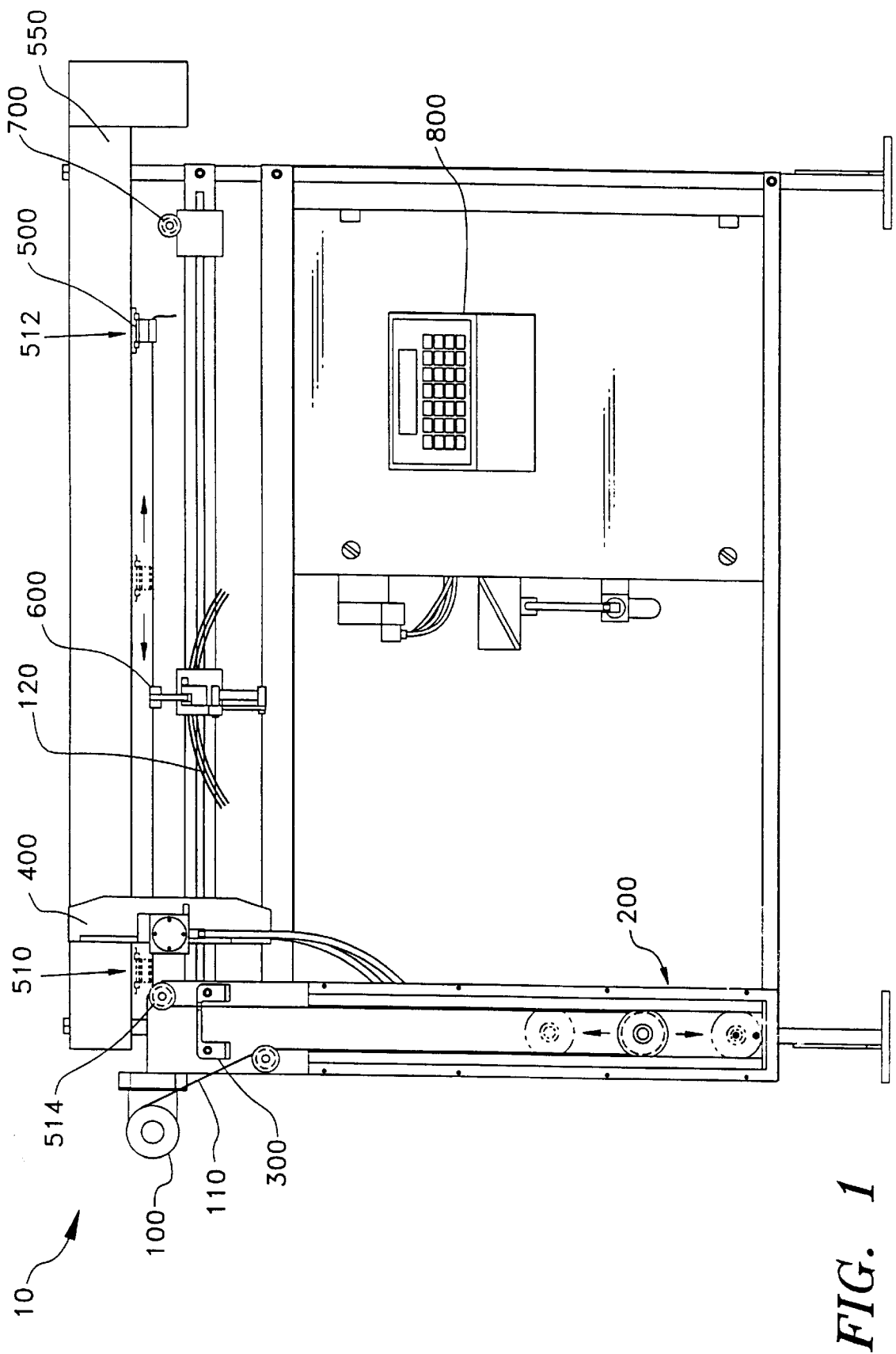
FIG. 1 is a schematic diagram showing a machine for thermally forming and cutting surgical sutures, in accordance with a preferred embodiment of the present invention.

Referring now to FIG. 1, there is shown a schematic diagram showing a machine 10 for thermally forming and cutting surgical sutures, in accordance with a preferred embodiment of the present invention. A continuous length of unfinished surgical suture material 110 is supplied to machine 10 from a supply spool 100 having unfinished surgical suture material 110 wound thereon. Unfinished surgical suture material 110 from supply spool 100 is initially advanced through a tensioning assembly 200 for creating a tension in the unfinished surgical suture material, and then through a knot detector system 300 for detecting whether a knot is present in any unfinished surgical suture material 110 passing through knot detector system 300. After passing through the knot detector system 300, the unfinished surgical suture material is advanced to a combined heating and cutting station 400, where (i) a predetermined length of the unfinished surgical suture material 110 is thermally formed into a length of surgical suture tip material, and (ii) the thermally formed surgical suture tip material is cut, thereby yielding a finished surgical suture 120 having a body portion formed of unfinished surgical suture material 110 and a thermally formed tip portion terminating with a cut end.

As explained more fully below, the unfinished surgical suture material 110 from supply spool 100 is advanced through machine 10 by a moving clamp 500 which is coupled to a linear actuator 550 for driving the moving clamp 500 between a starting or home position 510 on one side of the combined heating and cutting station 400 and an end position 512 on the other side of combined heating and cutting station 400. Moving clamp 500 has a grasping (or closed) state shown in FIG. 21, and a non-grasping (or open) state shown in FIG. 22. In accordance with instructions received from a controller 800, the moving clamp 500 selectively grasps and pulls the unfinished surgical suture material 110 through machine 10 in order to facilitate the manufacture of the finished surgical sutures 120. In addition to advancing unfinished surgical suture material through the machine, the moving clamp 500 functions to initially position and align the unfinished surgical suture material 110 within combined heating and cutting station 400.

Figure 23:
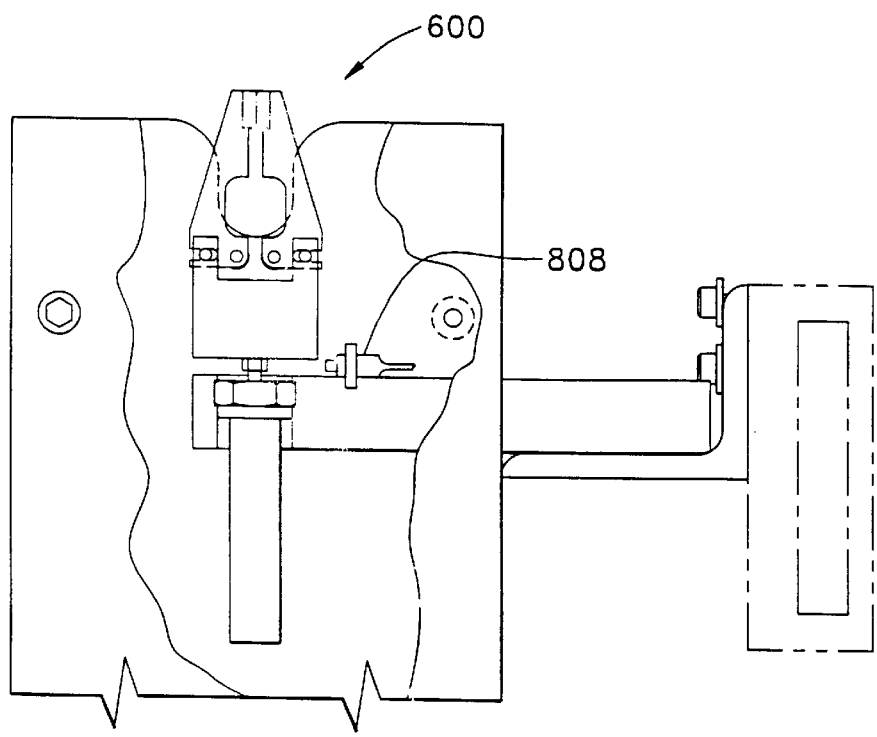
FIG. 23 is a cross-sectional view of a stationary clamp shown in its closed state for grasping surgical suture material, in accordance with a preferred embodiment of the present invention.

During operation of the machine 10, the moving clamp 500 initially grasps or closes on the unfinished surgical suture material 110 at the home position 510. Next, while the moving clamp 500 remains in its grasping or closed state, the linear actuator 550 drives the moving clamp 500 from its home position 510 to the end position 512. As the linear actuator 550 drives moving clamp 500 from its home position 510 to its position 512, the moving clamp 500 pulls a length of the unfinished surgical suture material 110 through the combined heating and cutting station 400 and through a stationary clamp 600 positioned between the end position 512 and the combined heating and cutting station 400. Like the moving clamp 500, the stationary clamp 600 has a grasping (or closed) state which is shown in FIG. 23, and a non-grasping (or open) state shown in FIG. 24. As the linear actuator 550 drives the moving clamp 500 from home position 510 to end position 512, the stationary clamp 600 is in its open state. After the moving clamp reaches its end position 512, the stationary clamp 600 grasps or closes on the unfinished surgical suture material 110 positioned within the stationary clamp 600. The position of stationary clamp 600 along the length of machine 10 may be adjusted in order to facilitate the creation of sutures with different lengths.

Figure 2:
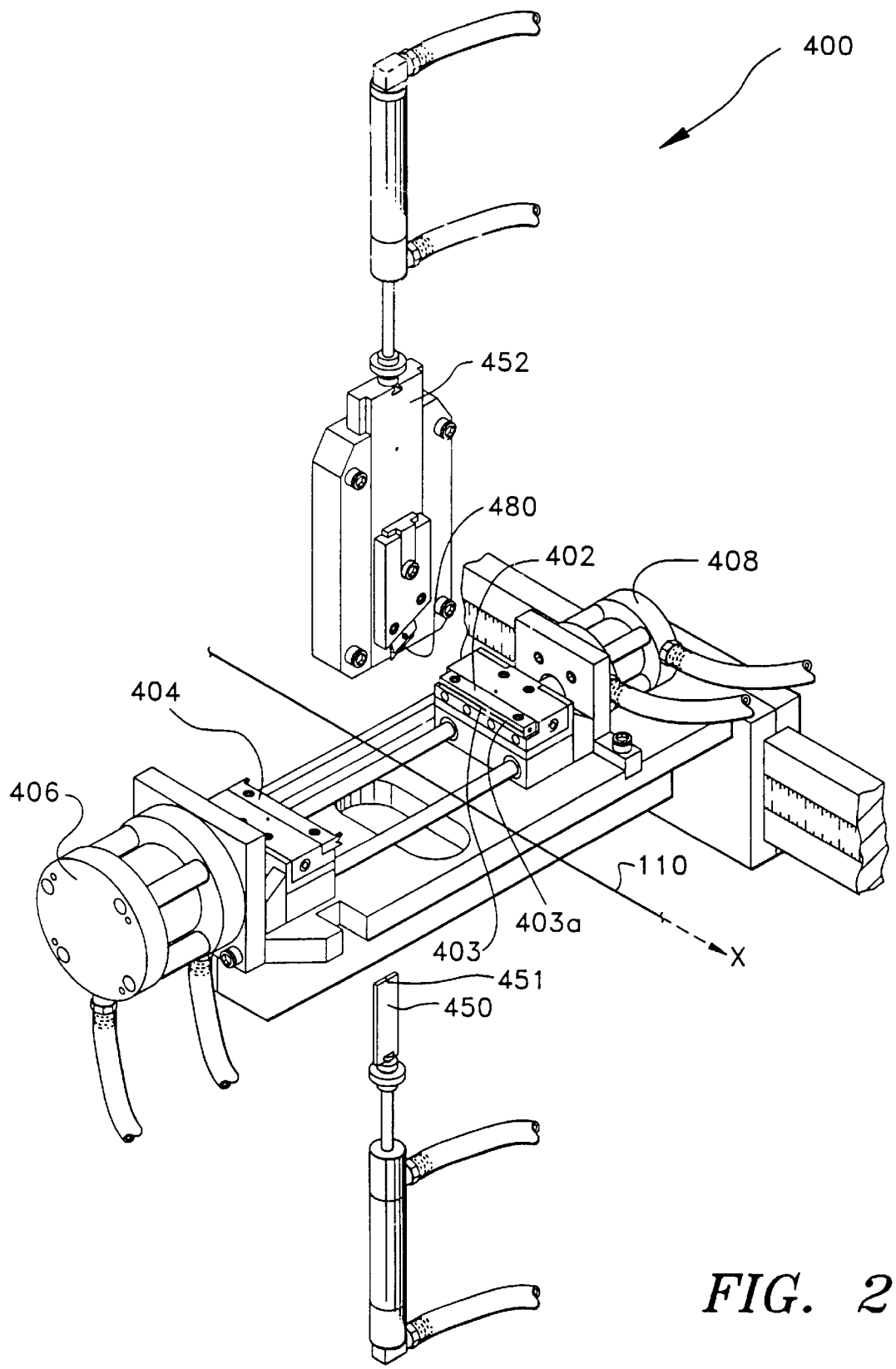
FIG. 2 is an isometric view of a suture tipping station formed from a pair of opposing heating dies both of which are in their retracted positions, in accordance with a preferred embodiment of the present invention.

As illustrated in FIG. 2, the combined heating and cutting station 400 includes a pair of opposing heating dies 402, 404, and a pair of opposing cutting dies 450, 452. The opposing heating dies 402, 404 have both an open and a closed state. Similarly, the opposing cutting dies 450, 452 have an open and a closed state. When, as described above, the linear actuator 550 drives the moving clamp 500 from home position 510 to end position 512, both the opposing heating die s 402, 404 and the opposing cutting dies 450, 452 in the combined heating and cutting station 400 are in their open positions. After the moving clamp reaches its end position 512 and the stationary clamp 600 has grasped or closed on the unfinished surgical suture material 110 positioned within the stationary clamp 600, the heating dies 402, 404 move from their open state to their closed state in order to thermally form a predetermined length of surgical suture tip material. The operation of the heating dies 402, 404 is described in greater detail below in connection with FIGS. 2–10. After the heating dies 402, 404 move from their open to their closed state, the moving clamp 500 releases the unfinished surgical suture material 112 in its grasp and, while the moving clamp is in its open or nongrasping state, the linear actuator 550 drives the moving clamp 500 from its end position 512 to its home position 510 where the moving clamp closes on a next piece of unfinished surgical suture material 110.

After the opposing heating dies 402, 404 have been in their closed state for a predetermined period of time, the heating dies 402, 404 move from their closed to their open state, thereby exposing a predetermined length of surgical suture tip material positioned between the opposing heating dies 402, 404. Next, while the surgical suture tip material remains positioned between the open heating dies 402, 404, the opposing cutting dies 450, 452 move from their open state to their closed state in order to "pinch" or firmly grasp the predetermined length of surgical suture tip material, preferably at a point adjacent to the midsection of the length of surgical suture tip material formed by the heating dies 402, 404. While the cutting dies 450, 452 are in their closed position, a cutting blade 480 is moved across a cross-section of the surgical suture tip material at a point adjacent to the cutting dies 450, 452, thereby yielding a thermally formed surgical suture tip with a cut end.

Thereafter, the cutting dies 450, 452 move from their closed position to their open position and the stationary clamp 600 releases the surgical suture material within its grasp. As the stationary clamp opens and releases the previously grasped surgical suture material, a finished surgical suture 120 having a thermally formed and cut tip falls by gravity onto an arm affixed to the stationary clamp 600. Prior to the time that the cutting dies 450, 452 are moved from their closed to their open position, the moving clamp 500 grasps or closes on the surgical suture material at home position 510, and the process described above is then preferably repeated in order to manufacture further finished surgical sutures 120. Since the tensioning assembly 200 exerts a tensioning force on the surgical suture material 110 positioned within machine 10, it is important for the moving clamp 500 to grasp or close on the surgical suture material at home position 510 prior to the time that the cutting dies 450, 452 are moved from their closed to their open position, in order to prevent the tensioning assembly 200 from pulling the trailing end of the surgical suture material cut by blade 480 in a reverse direction past home position 510 when the cutting dies 450, 452 are opened.

The unfinished surgical suture material 110 used in machine 10 for manufacturing the finished sutures 120 may consist of any thermoplastic braided suture material such as, for example, a polyester braided suture material, or a polyamide or polyolyfin suture material. In a preferred embodiment of the present invention described more fully below, the unfinished surgical suture material 110 used in machine 10 is a braided suture material formed of a polyethylene terephthalate, such as that sold by Ethicon, Inc. under the trademark ETHIBOND® EXCEL®. In a preferred embodiment, a Simatic model TI435 controller manufactured by Siemens is used to implement controller 800. An operator interface is preferably coupled to the controller 800.

Operation of Heating Dies

As mentioned above, after the moving clamp 500 has reached its end position 512 and the stationary clamp 600 has grasped or closed on the unfinished surgical suture material 110 positioned within the stationary clamp 600, the heating dies 402, 404 in the combined heating and cutting station 400 operate to thermally form a predetermined length of surgical suture tip material from the unfinished surgical suture material 110 positioned within the station 400. During the operation of the heating dies 402, 404, the unfinished surgical suture material 110 is suspended in an aligned and fixed positioned within station 400 by the stationary clamp 600 which is positioned on one side of station 400, and by the pulley 514 which is positioned on an opposing side of station 400. In addition, during the operation of the heating dies 402, 404, the unfinished surgical suture material 110 suspended within station 400 is maintained with a preset tension by tensioning system 200.

Figure 3:
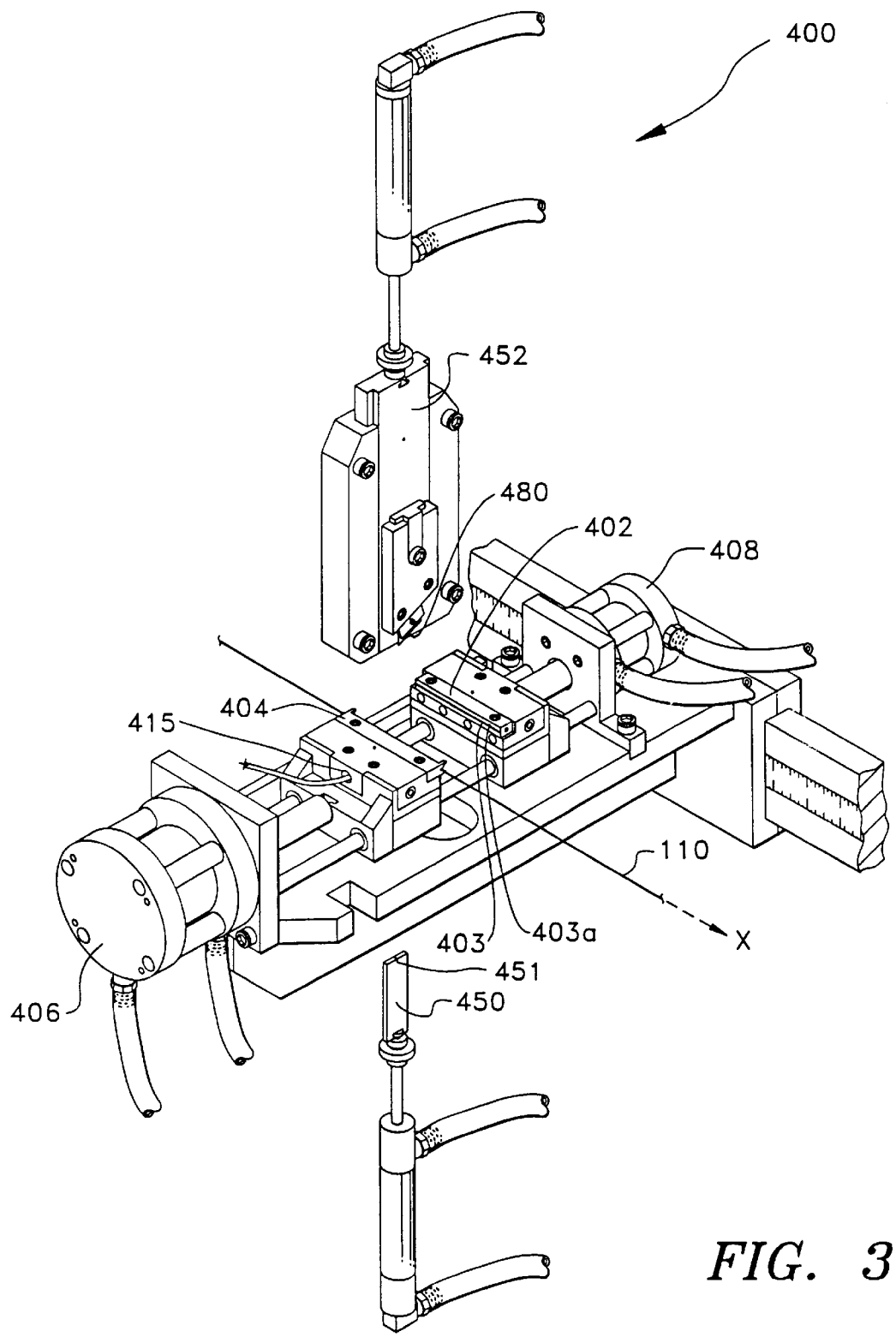
FIG. 3 is an isometric view of the suture tipping station of FIG. 2, wherein one of the heating dies in the station is in its retracted position and the other heating die in the station is in its extended position.
Figure 4:
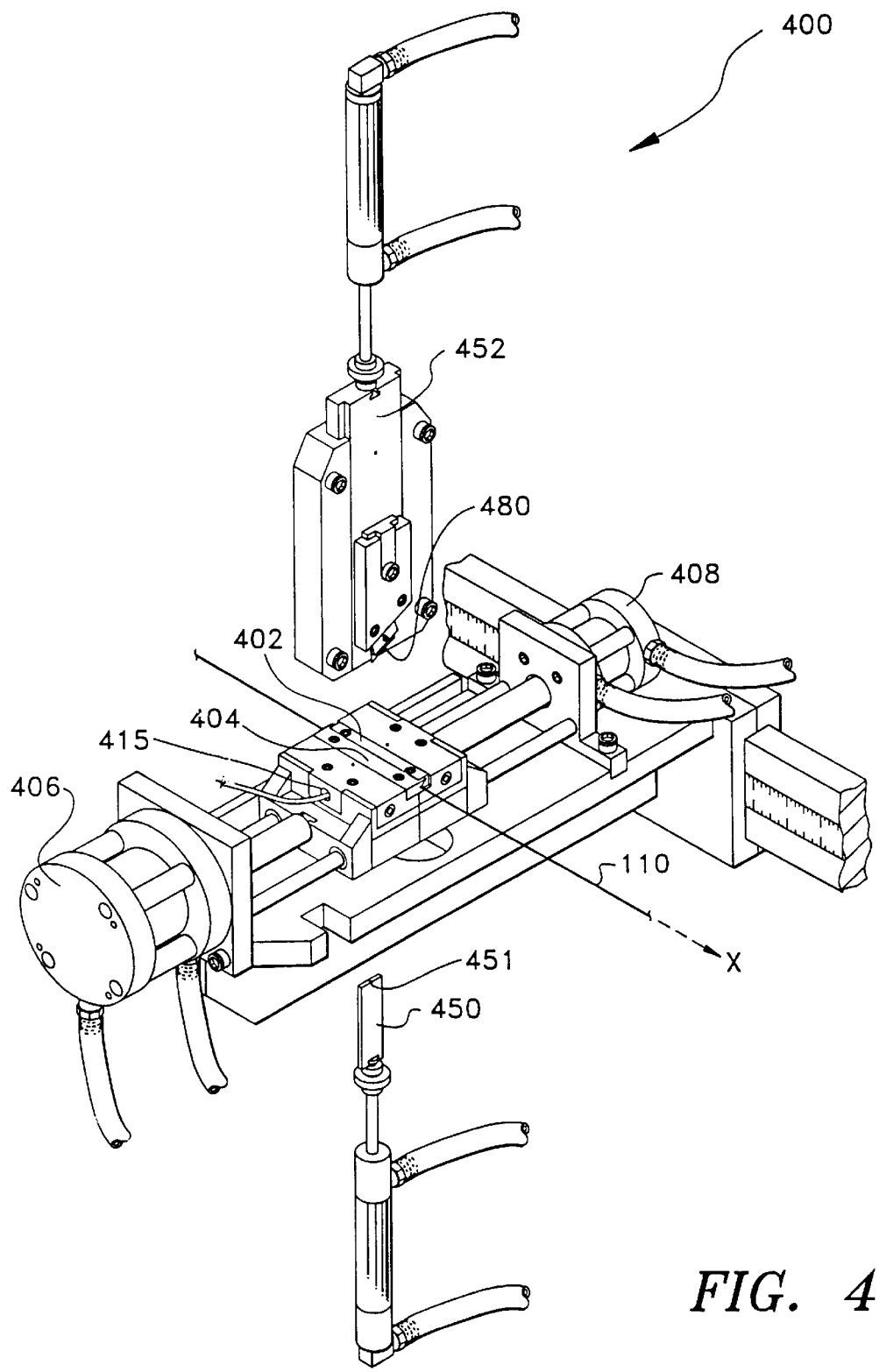
FIG. 4 is a further isometric view of the suture tipping station of FIG. 2, wherein both of the heating dies in the station are in their extended or closed positions.
Figure 5:
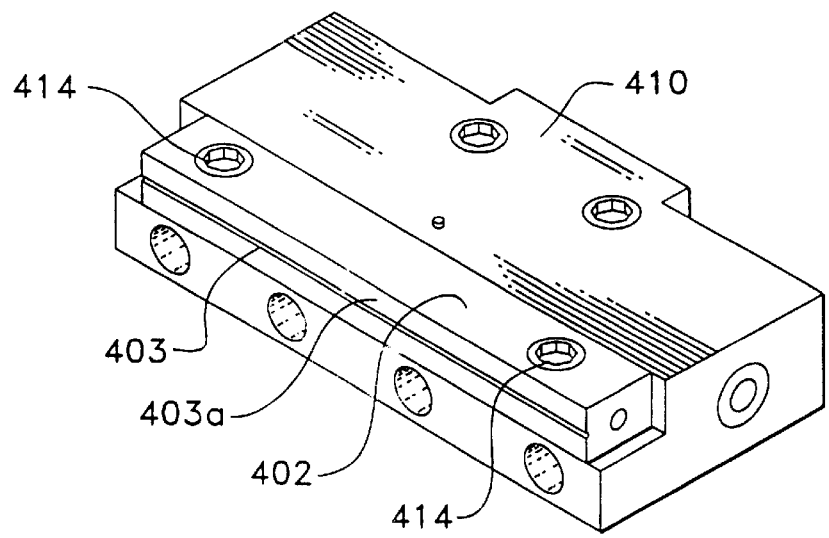
FIGS. 5 and 6 show isometric views of the opposing heating dies illustrated in FIGS. 2–4.
Figure 6:
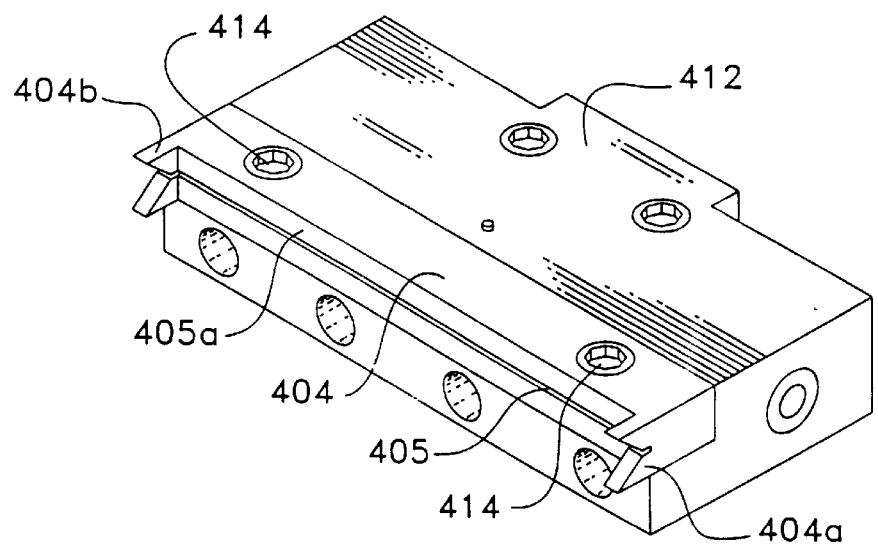

FIGS. 2–4 show three views of the combined heating and cutting station 400. Each of the views illustrates the position of the heating dies 402, 404 at a particular point during a suture tipping cycle. Referring now specifically to FIG. 2, there is shown an isometric view of station 400, wherein the heating dies 402, 404 are both in their retracted or open positions. FIG. 2 shows the position of heating dies 402, 404 when the moving 500 has reached its end position 512 and the stationary clamp 600 grasps or closes on the unfinished surgical suture material 110 positioned within the stationary clamp 600. After the moving clamp 500 has reached its end position 512 and the stationary clamp 600 has grasped or closed on the unfinished surgical suture material 110 positioned within the stationary clamp 600, a master cylinder 406 (controlled by controller 800) drives the heating die 404 from its retracted to its extended position. FIG. 3 shows the position of the heating dies 402, 404 after the master cylinder 406 has moved heating die 404 to its extended position. As the heating die 404 is moved to its extended position, a cross-sectional portion of the suture material 110 suspended within station 400 is received into a groove or channel 405 (shown in FIG. 6) within heating die 404. A pair of V-shaped guides 404a, 404b are affixed to the ends of the heating die 404 in order to facilitate the guidance of the unfinished suture material 110 into groove 405 during this step. In a preferred embodiment of the present invention, the master cylinder 406 causes the groove 405 in the heating die 404 to slightly overshoot (or pass) the centerline of the unfinished suture material 110 suspended within the station 400, in order to ensure that at least a cross-sectional portion of the unfinished suture material 110 is in fact received into the groove 405.

After the master cylinder 406 has moved heating die 404 to its extended position, a slave cylinder 408 (controlled by controller 800) drives heating die 402 from its retracted to its extended position. FIG. 4 shows the position of the heating dies 402, 404 after the slave cylinder 408 has moved heating die 402 to its extended position. As the heating die 402 is moved to its extended position, the cross-sectional portion of the suture material 110 which was not previously received into groove 405 is received into a groove or channel 403 (shown in FIG. 5) within heating die 402. After the slave cylinder 408 has driven heating die 402 to its extended position, the face 405a of heating die 404 stands adjacent to and abuts the face 403a of heating die 402. In a preferred embodiment of the present invention, the force used by slave cylinder 408 to drive heating die 402 to its extended position is less than the force used by master cylinder 406 to drive heating die 404 to its extended position. The use of a reduced force by the slave cylinder 406 insures that the position of the heating die 404 will not be disturbed when the heating die 402 is brought into contact with the heating die 404 as shown in FIG. 4. After faces 403a and 405a have been brought together and the heating dies 402, 404 have "closed on" the unfinished surgical suture material 110 as shown in FIG. 4, the heating dies 402, 404 remain in their closed or extended positions for a predetermined dwell time. Thereafter, the cylinders 406 and 408 open the heating dies 402, 404 by bringing them back to their initial retracted positions, thereby exposing a predetermined length of thermally formed surgical suture tip material suspended between opposing open heating dies 402, 404.

In the preferred embodiment of the present invention, the cross-sections of grooves 403 and 405 each represent a half circle or semi-circle such that, when faces 403a and 405a are brought into contact with each other as shown in FIG. 4, grooves 403 and 405 together form a singular cylindrical opening with a circular cross section (hereinafter "the heating die cross-section") running perpendicular to the axis of the cylindrical opening. The axis of the cylindrical opening formed by grooves 403 and 405 is aligned in parallel with the length of the surgical suture material 110 along the "x" axis (shown in FIGS. 2–4). In the preferred embodiment of the present invention, the diameter of the heating die cross-section is always less than the average cross-sectional size of the unfinished surgical suture material 110 provided from supply spool 100. By making the diameter of the heating die cross-section less than the average cross-sectional size of the unfinished surgical suture material 110, the present invention insures that grooves 403 and 405 both contact and apply pressure to the suture material 110 during the suture tipping process. The tension maintained in the unfinished surgical suture material 110 by tensioning assembly 200 functions to prevent the heating die cross-section from overly pinching or constricting the suture material during the suture tipping process.

Figure 7:
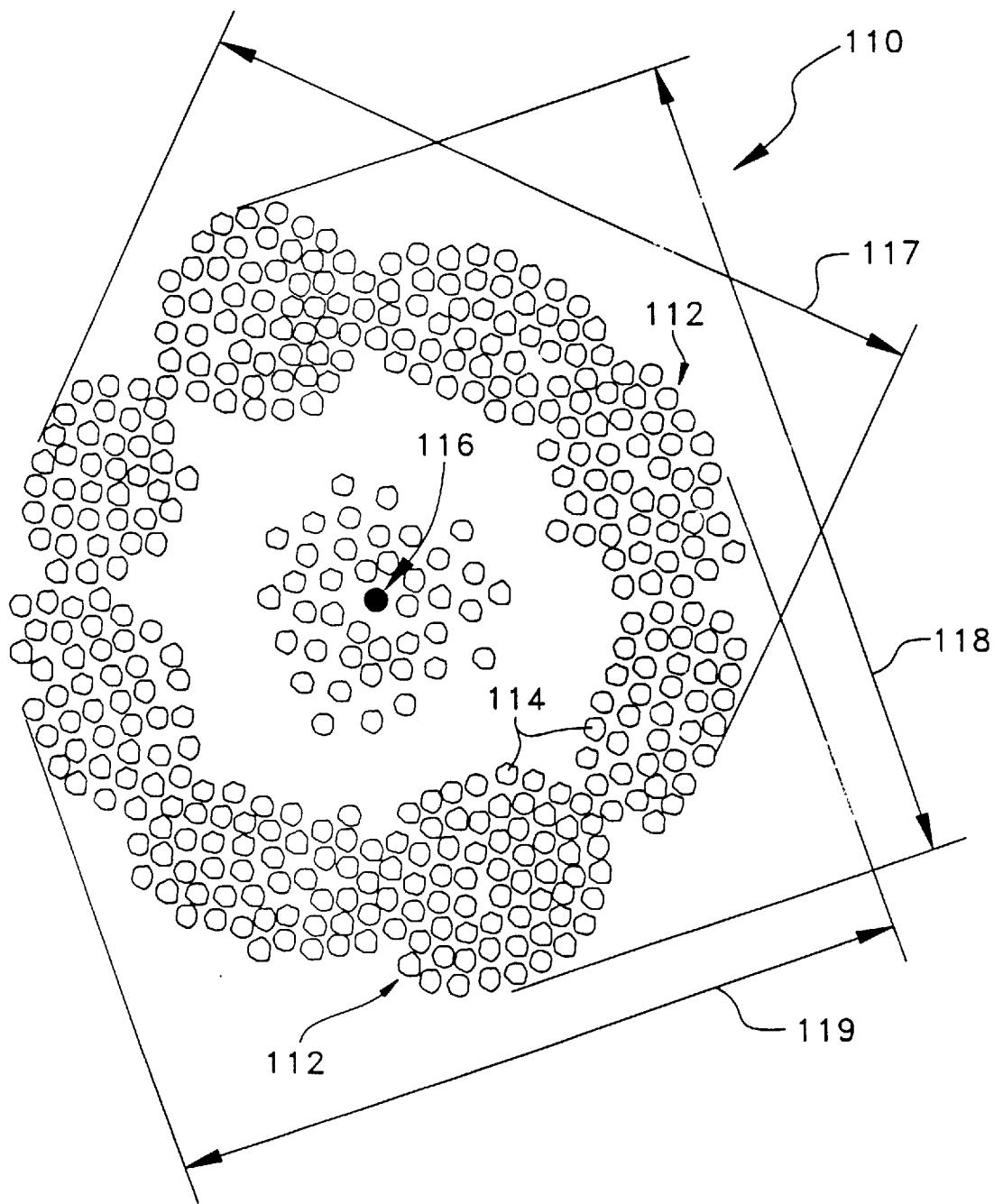
FIG. 7 is a cross-sectional view of an exemplary length of surgical suture material which has not been contacted by the heating dies of the heating station shown in FIGS. 2–4.
Figure 8:
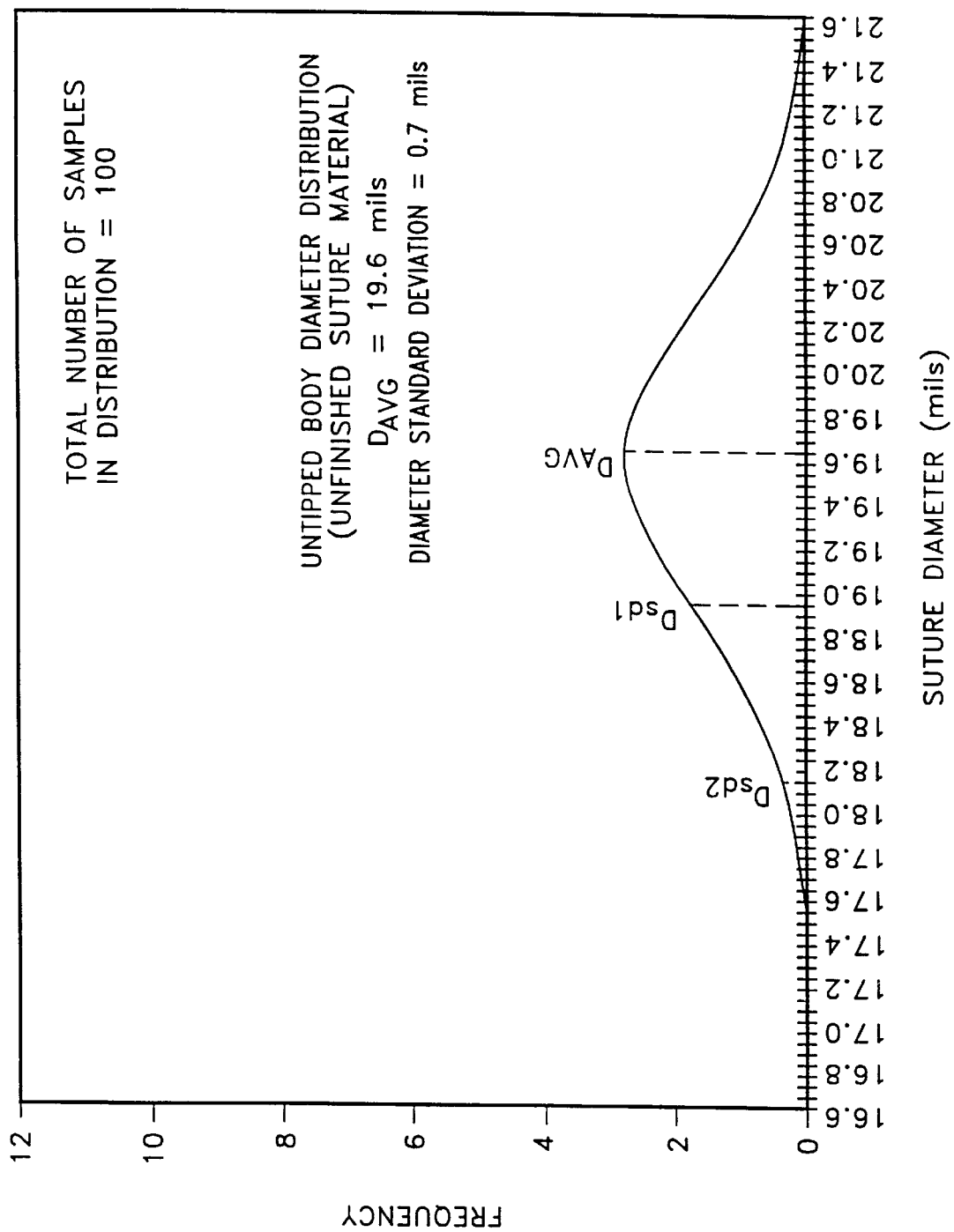
FIG. 8 is a graph illustrating the statistical distribution of the varying cross-sectional diameters found in the unfinished suture material depicted in FIG. 7.

Referring now to FIG. 7, there is shown a cross-sectional view of an exemplary length of unfinished surgical suture material 110 which has not been contacted by the heating dies 402, 404 of station 400. Unfinished suture material 110 (as shown in FIG. 7) is used to form the untipped body portions of sutures made in accordance with the present invention. Unfinished suture material 110 is formed of a plurality of yarns 112, each of which is formed from several strands or filaments 114. Since unfinished suture material 110 is braided, its cross-section is not uniformly circular. On the contrary, the diameter of the cross-section of the unfinished suture material 110 varies depending on the position of the diameter measured. Thus, the three exemplary diameter measurements 117, 118, 119 of the suture material 110 shown in FIG. 7, all of which pass through the centroid 116 of the cross-section, each have a different length. FIG. 8 shows a graph illustrating the statistical distribution of the varying cross-sectional diameters found in the unfinished suture material depicted in FIG. 7, and, in particular, the varying cross-sectional diameters found in unfinished size 0 ETHIBOND® EXCEL® surgical suture material. As shown in FIG. 8, for a given length of unfinished surgical suture material 110, there is an average cross-sectional diameter ($D_{avg}$), a first standard deviation cross-sectional diameter ($D_{sd1}$) representing a cross-sectional diameter length that is one standard deviation below $D_{avg}$, and a second standard deviation cross-sectional diameter ($D_{sd2}$) representing a cross-sectional diameter length that is two standard deviations below $D_{avg}$.

In a first preferred embodiment of the present invention, the diameter of the heating die cross-section formed by grooves 403 and 405 is a constant that is less than the $D_{avg}$ value for the unfinished suture material 110; in a second preferred embodiment of the present invention, the diameter of the heating die cross-section formed by grooves 403 and 405 is a constant that is about equal to the $D_{sd1}$ value for the unfinished suture material 110; and in a still further preferred embodiment of the present invention, the diameter of the heating die cross-section formed by grooves 403 and 405 is a constant that is about equal to the $D_{sd2}$ value for the unfinished suture material 110.

Figure 9:
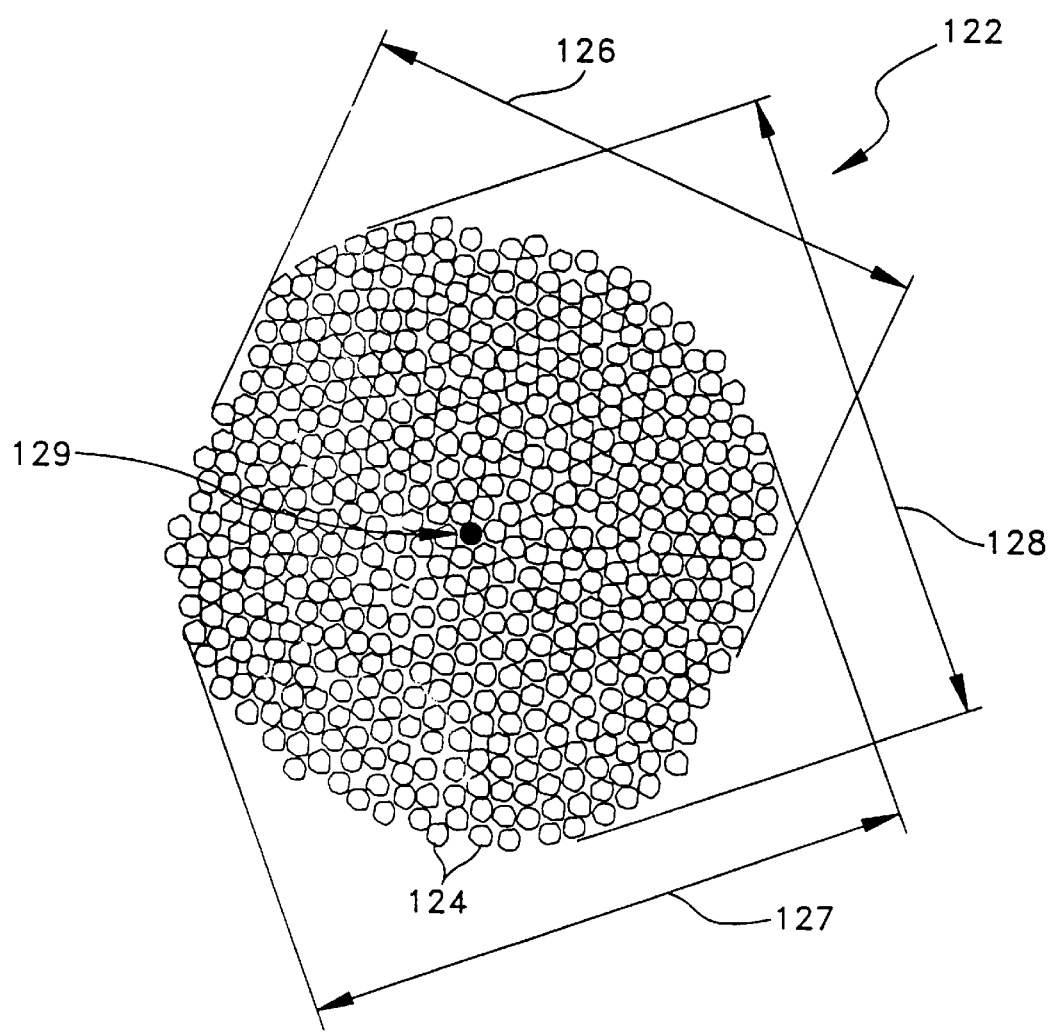
FIG. 9 is a cross-sectional view of an exemplary length of a surgical suture tip which has been thermally formed by the heating dies of the heating station shown in FIGS. 2–4, in accordance with a preferred embodiment of the present invention.

Referring now to FIG. 9, there is shown a cross-section 122 of an exemplary length of a surgical suture tip that has been thermally formed by the heating dies 402, 404 of station 400 as described above in connection with FIGS. 2–4. The exemplary cross-section 122 shown in FIG. 9 was thermally formed (or finished) using a heating die cross-section having a constant diameter that was about equal to the $D_{sd2}$ value for the unfinished suture material 110 initially supplied to station 400. As a result of the fact that the diameter of the heating die cross-section was less than the $D_{avg}$ value for the unfinished suture material 110, the unfinished suture material 110 was contacted by the heating dies 402, 404 during the thermal heat tipping process. The contacting of the heating dies 402, 404 with the unfinished suture material 110 during the thermal heat tipping process, together with the fact that the suture material 110 is under tension during this process, causes the suture material 110 which is contacted by the heating dies 402, 404 to be compressed, thereby resulting in the "rounding" of filaments (such as filaments 124) positioned about the perimeter of cross-section 122. As a result of this "rounding" of the filaments about its perimeter, the cross-section 122 is generally uniform in diameter. In contrast to the varying diameters of the cross-section of the unfinished suture material 110 shown in FIG. 7, the diameters of the cross-section 122 are generally constant irrespective of the position of the diameter measured. Thus, the three exemplary diameter measurements 126, 127, 128 of the cross-section 122 shown in FIG. 9, all of which pass through the cross-section, each have about the same length. Tables I, II, and III illustrate cross-sectional diameters of size 0, 2/0 and 3/0 sutures having body portion formed from unfinished ETHIBOND® EXCEL® suture material and tip portions which have been formed by dies 402,404 (having a constant cross-sectional diameter about equal to the $D_{sd2}$ value of the unfinished suture material), in accordance with the present invention. As these tables show, the present invention result in sutures having tip portions (110a) with a cross-section that is both smaller in diameter and more uniform (i.e., smaller diameter standard deviation) than the unfinished suture body portions (110b) adjacent to such tip portions.

TABLE I

Size Measurements of Tip and Body Diameters of Size 0 Sutures

| BODY/TIP END DIAMETER | | SET 1 | | SET 2 | |
|---|---|---|---|---|---|
| | | TIP END MILS | BODY MILS | TIP END MILS | BODY MILS |
| SAMPLE# | 1 | 17.44 | 18.97 | 17.92 | 20.85 |
| | 2 | 17.64 | 20.40 | 17.82 | 19.41 |
| | 3 | 17.29 | 18.45 | 18.10 | 20.08 |
| | 4 | 17.52 | 18.96 | 17.70 | 19.56 |
| | 5 | 17.59 | 19.38 | 17.63 | 19.43 |
| | 6 | 17.82 | 19.47 | 17.82 | 20.70 |
| | 7 | 17.90 | 19.74 | 17.45 | 18.57 |
| | 8 | 17.57 | 20.47 | 18.20 | 19.31 |
| | 9 | 17.43 | 20.44 | 17.70 | 19.83 |
| | 10 | 17.61 | 20.07 | 17.90 | 19.27 |
| AVERAGE | | 17.58 | 19.63 | 17.82 | 19.70 |
| STANDARD DEV | | 0.18 | 0.71 | 0.22 | 0.69 |

TABLE II

Size Measurements of Tip and Body Diameters of Size 2/0 Sutures

| BODY/TIP END DIAMETER | | SET 1 | | SET 2 | |
|---|---|---|---|---|---|
| | | TIP END MILS | BODY MILS | TIP END MILS | BODY MILS |
| SAMPLE# | 1 | 14.78 | 16.66 | 15.39 | 17.70 |
| | 2 | 14.98 | 17.74 | 14.55 | 15.93 |
| | 3 | 15.03 | 16.84 | 14.87 | 15.87 |
| | 4 | 15.04 | 17.44 | 14.92 | 16.91 |
| | 5 | 15.14 | 16.54 | 14.74 | 17.15 |
| | 6 | 15.19 | 16.71 | 14.61 | 16.07 |
| | 7 | 14.97 | 17.05 | 15.24 | 20.01 |
| | 8 | 14.86 | 15.41 | 14.75 | 17.53 |
| | 9 | 15.04 | 17.17 | 14.61 | 16.39 |
| | 10 | 14.89 | 18.57 | 14.85 | 17.12 |
| AVERAGE | | 14.99 | 17.01 | 14.85 | 17.07 |
| STANDARD DEV. | | 0.12 | 0.83 | 0.27 | 1.22 |

TABLE III

Size Measurements of Tip and Body Diameters of Size 3/0 Sutures

| BODY/TIP END DIAMETER | | SET 1 | | SET 2 | |
|---|---|---|---|---|---|
| | | TIP END MILS | BODY MILS | TIP END MILS | BODY MILS |
| SAMPLE# | 1 | 11.87 | 15.27 | 11.73 | 13.31 |
| | 2 | 11.84 | 13.82 | 12.00 | 12.98 |
| | 3 | 11.66 | 14.05 | 11.80 | 13.47 |
| | 4 | 11.89 | 15.40 | 11.64 | 13.37 |
| | 5 | 11.63 | 15.93 | 11.65 | 13.08 |
| | 6 | 11.55 | 15.01 | 11.68 | 13.53 |
| | 7 | 11.56 | 14.60 | 11.37 | 12.82 |
| | 8 | 11.77 | 14.98 | 11.45 | 13.79 |
| | 9 | 11.66 | 13.85 | 11.66 | 13.39 |
| | 10 | 11.66 | 13.89 | 11.65 | 13.10 |
| AVERAGE | | 11.71 | 14.68 | 11.66 | 13.28 |
| STANDARD DEV. | | 0.12 | 0.75 | 0.17 | 0.29 |

Figure 10:
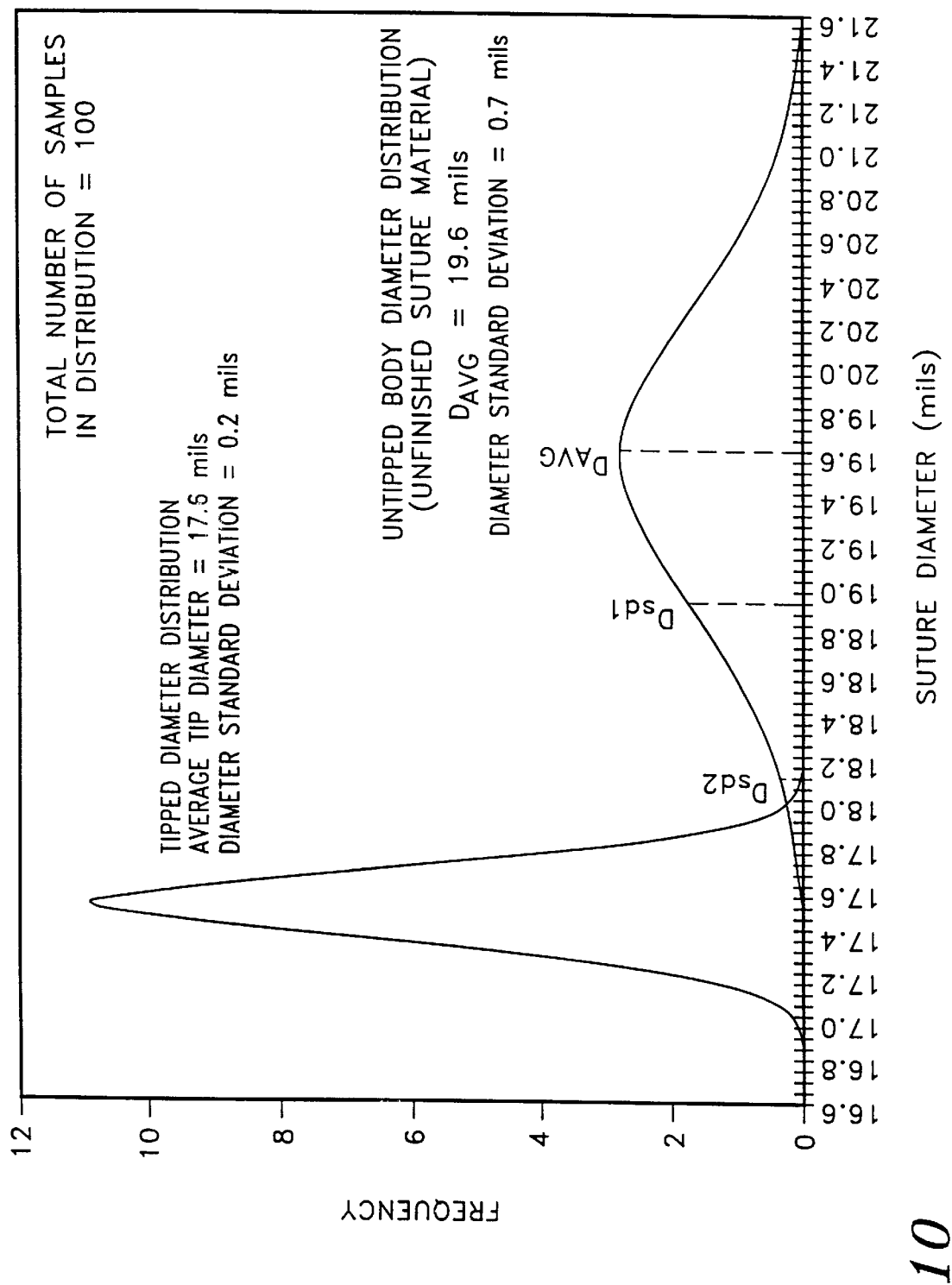
FIG. 10 is a graph illustrating the statistical distribution of the generally uniform cross-sectional diameters found in the thermally formed suture tip depicted in FIG. 9 and the statistical relationship between these generally uniform tip diameters and the varying cross-sectional diameters found in the body portion of a suture made in accordance with a preferred embodiment of the present invention.

FIG. 10 shows a graph illustrating the statistical distribution of the generally uniform cross-sectional diameters found in the thermally formed suture tip depicted in FIG. 9 and exemplified by Table I above. As shown in FIG. 10, the suture tip produced by the heating dies of the present invention has a generally uniform cross-sectional diameter which centers about the heating die cross-section (in this case $D_{sd2}$), and which is less than the $D_{avg}$ value corresponding to the unfinished suture material 110 supplied to station 400 and forming the untipped body portion of the resulting suture.

Since the heating die cross-section used in the present invention varies depending upon the $D_{avg}$ value of the unfinished suture material 110 being supplied to machine 10, the heating dies 402, 404 are secured to heater manifolds 410, 412, respectively, by removable screws 414, which allow an operator to change the heating dies 402, 404 being used in station 400 depending on the size of the suture material 110 being used. A thermocouple 415 for heating the removable heating dies 402, 404 is positioned in each of the manifolds 410, 412 and coupled to controller 800. Thus, for larger diameter suture material 110, the operator will use heating dies 402, 404 which form a greater heating die cross-section than dies used for thermally forming tips on smaller diameter suture material. Set forth in Table IV below are the preferred heating die cross-section diameters used for thermally forming tips on different sizes of an unfinished braided suture material formed of a polyethylene terephthalate, such as that sold by Ethicon, Inc. under the trademark ETHIBOND® EXCEL®. Also set forth in Table IV below are the preferred temperatures that heating dies 402, 404 should be maintained at during the heat tipping process, the preferred tensions at which the sutures should be maintained during the heat tipping process, and the preferred dwell times during which the heating dies 402, 404 should remain closed on the unfinished suture material 110 during the heat tipping process.

TABLE IV

| SIZE OF UN- FINISHED SUTURE MATERIAL | 0 | 2/0 | 3/0 | 4/0 | 5/0 |
|---|---|---|---|---|---|
| Heating Die Cross-Section Diameter (in mils) | 17.70 | 15.00 | 11.40 | 9.00 | 6.85 |
| Heating Die Temperature (in °C.) | 246–250 | 246–250 | 246–250 | 246–250 | 246–250 |
| Heating Die Dwell Time (in seconds) | 2.6–3.0 | 2.6–3.0 | 2.6–3.0 | 2.4–2.8 | 2.0–2.4 |
| Tension (in grams) | 100–120 | 100–120 | 100–120 | 40–60 | 40–60 |

In the preferred embodiment of the present invention, heating dies 402, 404 are made of steel, and are coated with a non-stick substance such as TEFLON® (polytetrafluoroethylene polymer) or NEDOX®, manufactured by General Magnaplate, in order to facilitate the release of the suture material from the grooves 403, 405 when the heating dies 402, 404 are opened. Although in the preferred embodiment described above, the heating die cross-section formed by grooves 403, 405 was circular in shape, it will be understood by those skilled in the art that heating die cross-sections defining other geometric shapes may also be used in conjunction with the present invention.

Operation of Cutting Dies

After the cylinders 406 and 408 open the heating dies 402, 404 by bringing them back to their initial retracted positions, thereby exposing a predetermined length of thermally formed surgical suture tip material suspended between opposing open heating dies 402, 404, the cutting dies 450, 452 in the combined heating and cutting station 400 operate to cut the thermally formed length of surgical suture tip material. When the present invention is used to create finished suture material for "double-armed" sutures (i.e., sutures having needles at both ends of each suture), the thermally formed length of surgical suture tip material is preferably cut at its midpoint; otherwise the thermally formed length of surgical suture tip material is preferably cut near one of its ends. During the initial operation of the cutting dies 450, 452, the surgical suture material suspended in station 400 remains in the same position that it occupied during the thermal tipping process described above. Thus, the surgical suture material remains positioned and aligned along axis "x". In addition, during the initial operation of the cutting dies 450, 452, the surgical suture material suspended within station 400 is maintained at the same present tension that was used during the thermal tipping process described above.

Figure 11:
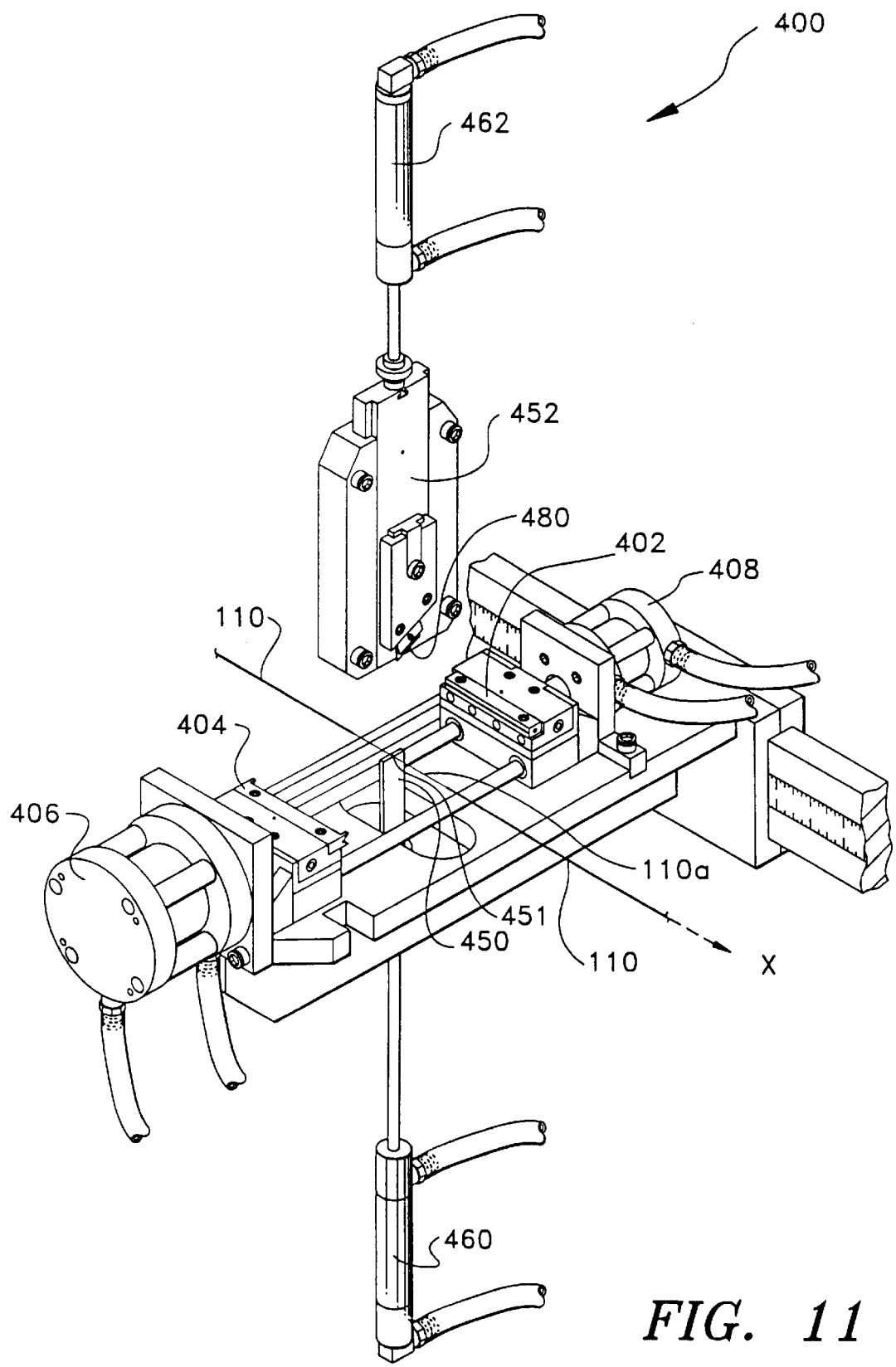
FIG. 11 is an isometric view of a suture cutting station formed from a pair of opposing cutting dies, wherein one of the cutting dies is in its retracted position and the other cutting die is in its extended position, in accordance with a preferred embodiment of the present invention.
Figure 12:
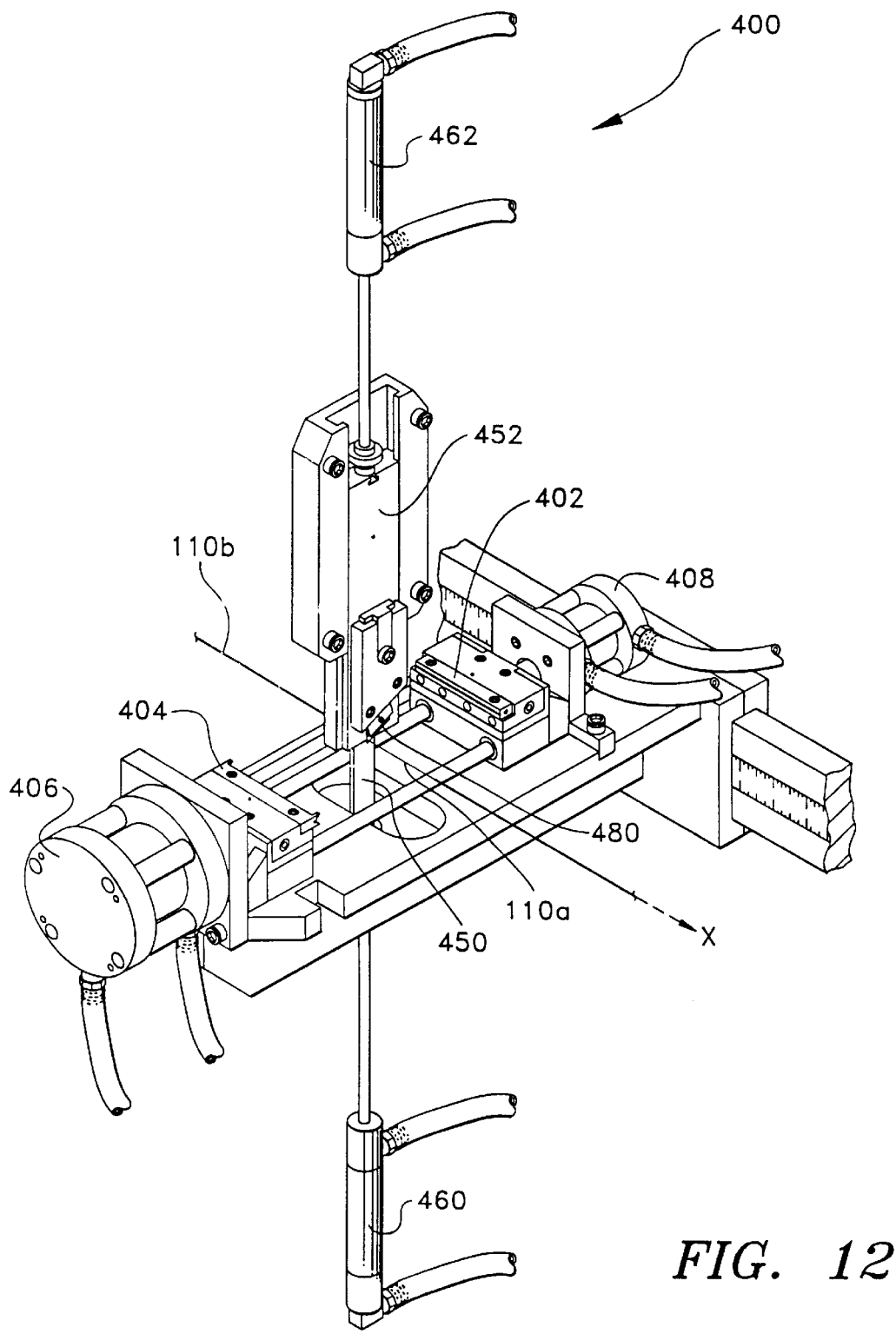
FIG. 12 is an isometric view of the suture cutting station of FIG. 11, wherein both of the cutting dies in the station are in their extended or closed positions, in accordance with a preferred embodiment of the present invention.
Figure 13:
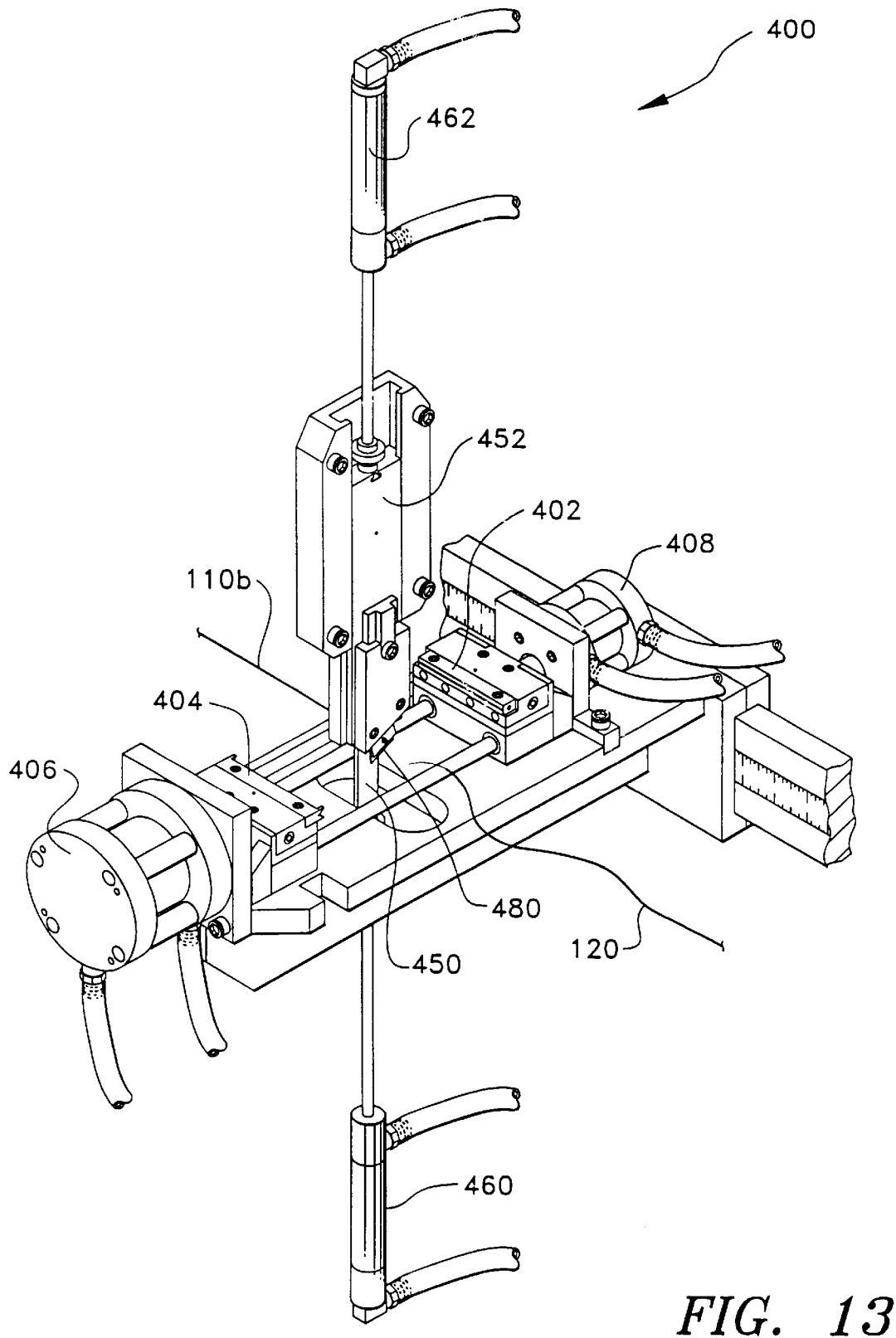
FIG. 13 is an isometric view of the suture cutting station of FIG. 12, illustrating the position of the cutting dies in the station as a cutting blade moves through a cross-section of thermally formed surgical suture material positioned in the cutting station, in accordance with a preferred embodiment of the present invention.
Figure 15:
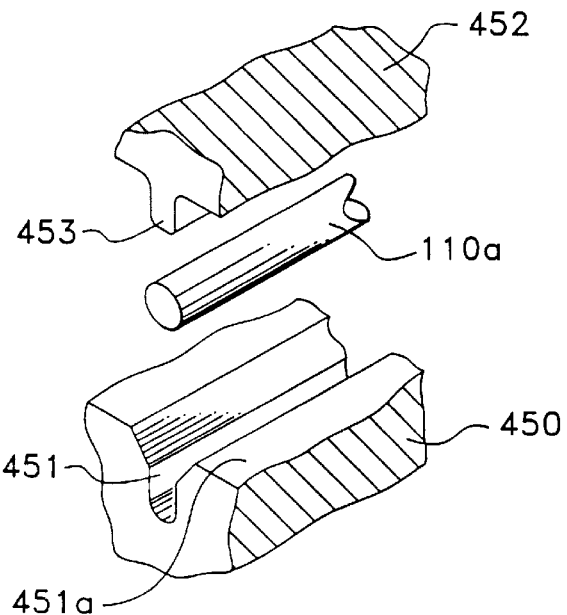
FIG. 15 is an exploded isometric view of the opposing cutting dies shown in FIGS. 12–13.

FIGS. 11–13 show three further views of the combined heating and cutting station 400. Each of the views illustrates the position of the cutting dies 450, 452 and the cutting blade 480 at a particular point during a suture cutting cycle. During the thermal tipping cycle described above, both of the cutting dies 450, 452 remained in their open or retracted positions. Following the opening of heating dies 402, 404 at the end of the thermal tipping cycle, a master cylinder 460 (controlled by controller 800) drives the cutting die 450 from its retracted to its extended position. FIG. 11 shows the position of the cutting dies 450, 452 after the master cylinder 460 has moved cutting die 450 to its extended position. As the cutting die 450 is moved to its extended position, a cross-section of the thermally tipped suture material 110a suspended within station 400 is received into a groove or channel 451 (shown in FIGS. 15–16) within cutting die 450. A pair of V-shaped guides (not shown) may be affixed to the ends of the cutting die 450 in order to facilitate the guidance of the thermally tipped suture material 110a into groove 451 during this step. In a preferred embodiment of the present invention, the master cylinder 460 causes the groove 451 in the cutting die 450 to slightly overshoot the location of the thermally tipped suture material 110a suspended within the station 400, in order to ensure that the entirety of a cross-sectional portion of the thermally tipped suture material 110a is in fact received into the groove 451 (as shown in FIG. 17).

Figure 14:
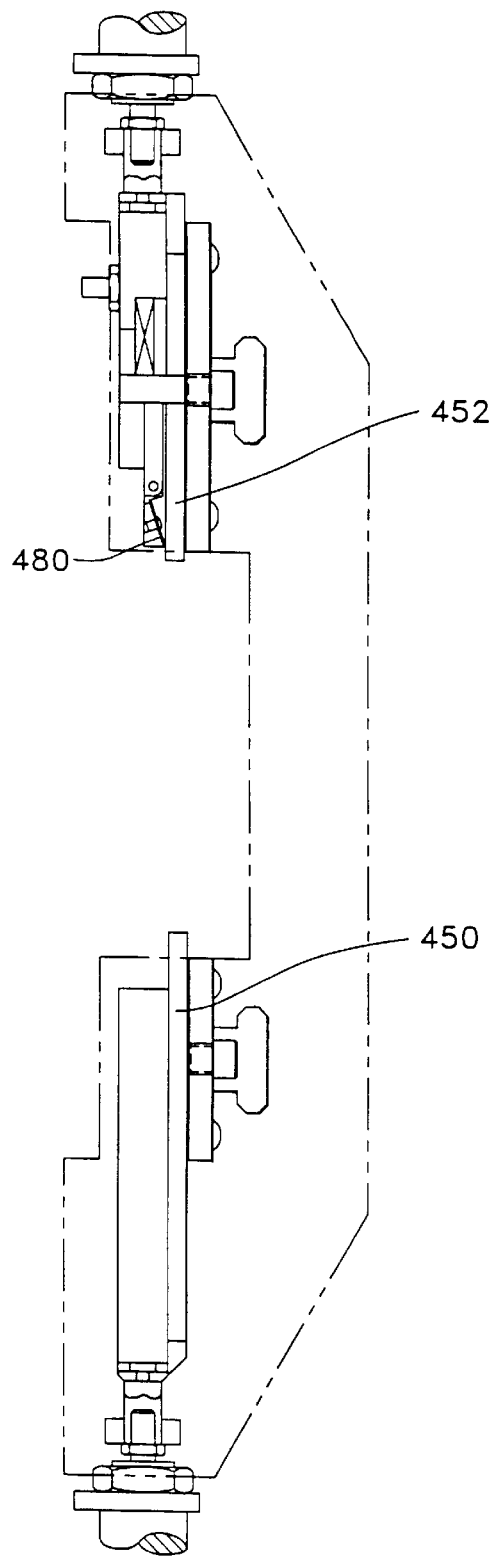
FIG. 14 is a cross-sectional view showing the components of the suture cutting station of FIGS. 11–13.

After the master cylinder 460 has moved the cutting die 450 to its extended position, a mechanical activator such as a slave cylinder 462 (also controlled by controller 800) drives the cutting die 452 from its retracted to its extended position. FIG. 12 shows the position of the cutting dies 450, 452 after the slave cylinder 462 has moved cutting die 452 to its extended position. After the slave cylinder 462 has driven cutting die 452 to its extended position, the face 451a of cutting die 450 stands adjacent to and abuts the face 453a of cutting die 452. The cutting die 452 includes a square-shaped notch (or boss) 453 which is received into groove 451 when faces 451a and 453a are brought together. In a preferred embodiment of the present invention, the force used by slave cylinder 462 to drive cutting die 452 to its extended position is less than the force used by master cylinder 460 to drive cutting die 450 to its extended position. The use of a reduced force by the slave cylinder 462 insures that the position of the cutting die 450 will not be disturbed when the cutting die 452 is brought into contact with the cutting die 450 as shown in FIG. 12. After faces 451a and 453a have been brought together and the cutting dies 450, 452 have "closed on" the thermally tipped suture material 110a as shown in FIG. 17, blade 480 is moved by slave cylinder 462 across the thermally tipped suture material 110a in a direction perpendicular to the axis "x", thereby shearing the thermally tipped suture material 110a material 110a at a point adjacent to the cutting dies 450, 452 and creating a finished suture 120 having a body portion formed of unfinished surgical suture material 110 and a thermally formed tip portion terminating with a cut end. FIG. 13 illustrates the positions of the cutting dies 450, 452 as the cutting blade 480 slices through the thermally tipped suture material 110a, and FIG. 14 shows the proximity of the cutting blade 480 to the cutting dies 450, 452 which is maintained during the cutting process. Following the slicing of the thermally tipped suture material 110a, cylinders 460 and 462 open the cutting dies 450, 452 by bringing them back to their initial retracted positions. As mentioned above, prior to the opening of the cutting dies 450, 452 at the end of the cutting cycle, the moving clamp 500 grasps or closes on the surgical suture material 110 at home position 510, in order to prevent the tensioning assembly 200 from pulling the trailing end 110b of the surgical suture material cut by blade 480 in a reverse direction past home position 510 when the cutting dies 450, 452 are opened.

Figures 16, 17:
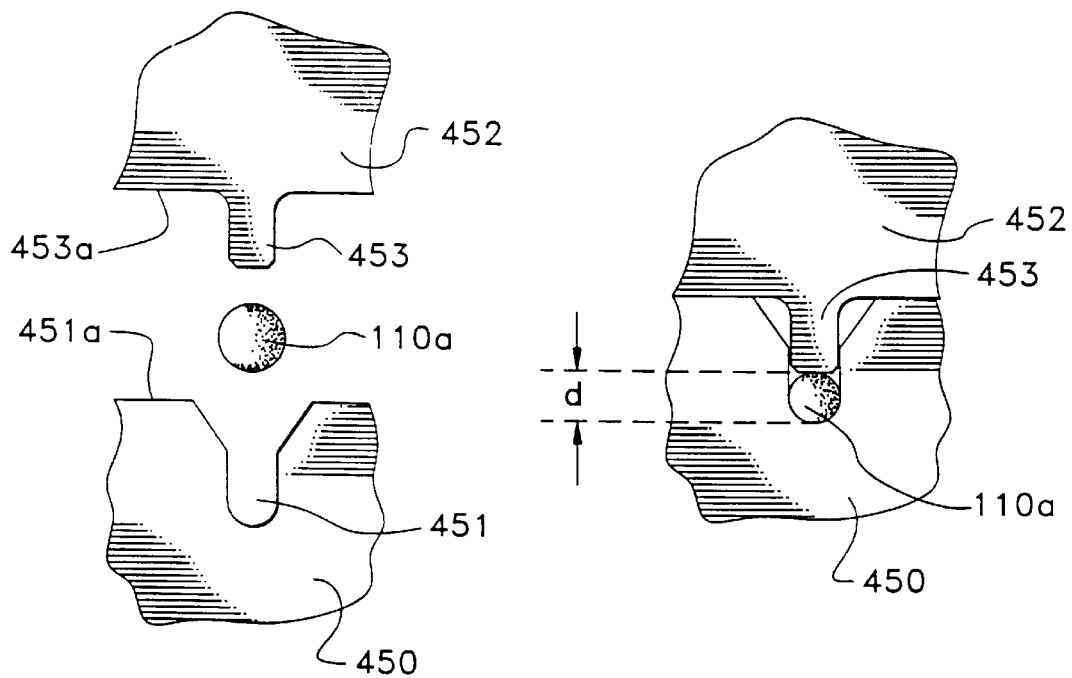
FIG. 16 is an exploded front elevational view of the opposing cutting dies shown in FIG. 15.
FIG. 17 is a front elevational view of the opposing cutting dies of FIGS. 15–16, in accordance with a preferred embodiment of the present invention.

In the preferred embodiment of the present invention, the cross-sections of groove 451 and notch 453 are such that, when faces 451a and 453a are brought into contact with each other as shown in FIG. 17, groove 451 and notch 453 together form a singular cutting die opening aligned along the "x" axis with a cross-section (hereinafter "the cutting die cross-section") running perpendicular to the "x" axis. Thus, the axis of the cutting die opening formed by groove 450 and notch 452 is aligned in parallel with the length of the thermally tipped surgical suture material 110a along the "x" axis. In the preferred embodiment of the present invention, the diameter "d" (shown in FIG. 17) of the cutting die cross-section is always less than the diameter of the heating die cross-section used for thermally forming the tipped suture material 110a. By making the diameter of the cutting die cross-section less than the diameter of the heating die cross-section, the present invention insures that groove 451 and notch 453 not only contact, but also firmly hold or pinch the thermally tipped suture material 110a positioned between the cutting dies 450, 452 during the suture cutting process. By firmly holding or pinching the thermally tipped suture material 110a at a point directly adjacent to the location where blade 480 slices through the suture material 110a, the cutting mechanism of the present invention yields a suture with an extremely precise cut end which, among other things, facilitates the later insertion of the cut end into a needle.

Alternative Preferred Cutting Die Mechanism

Figure 18:
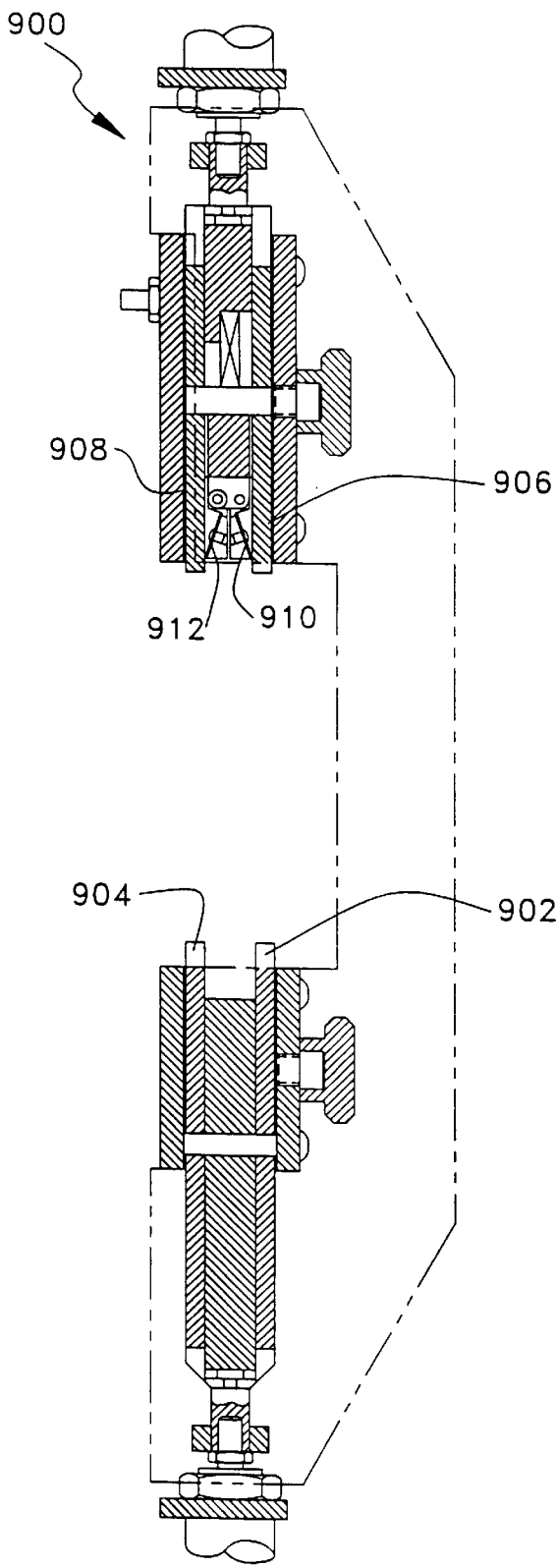
FIG. 18 is a cross-sectional view of a suture cutting station for simultaneously cutting a length of thermally formed surgical suture material at two different locations, in accordance with an alternative preferred embodiment of the present invention.
Figure 19:
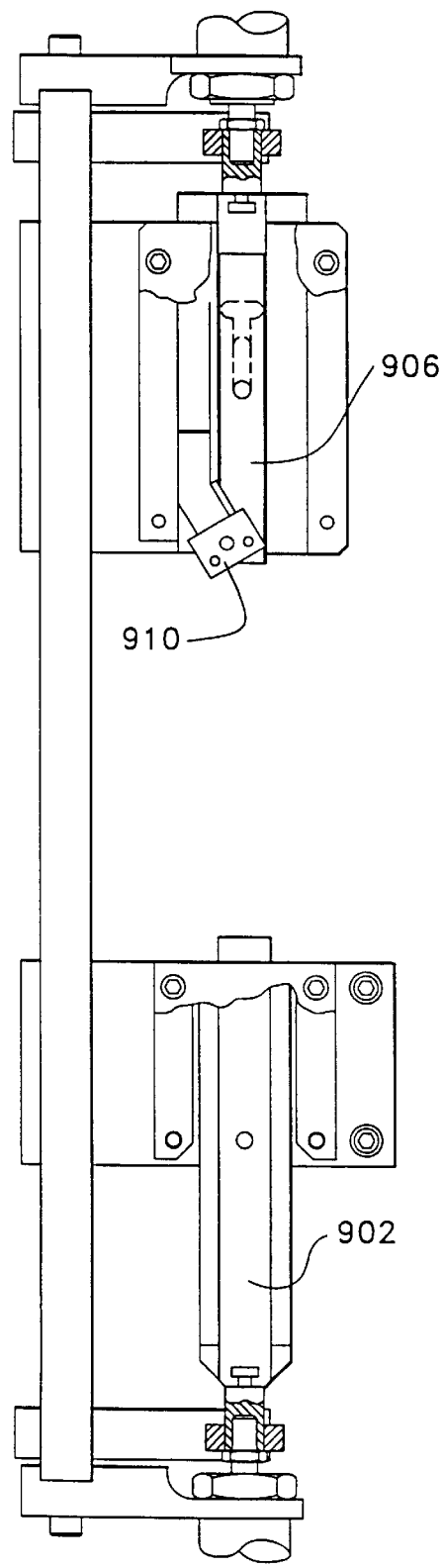
FIG. 19 is a side view of the suture cutting station shown in FIG. 18.

The cutting die system described above in conjunction with FIGS. 11–17 is advantageous for creating single-armed sutures which have a needle attached at only one end. However, for some surgical procedures, double-armed sutures which have a needle attached at each end are required. In order to manufacture suture material that can be used for making double-armed sutures, it is important for both ends of the suture material to be formed from precise cuts, so that each end of the suture can be inserted into a needle. An alternative cutting die system 900 shown in FIGS. 18–19 may be used in place of the cutting die system shown in FIGS. 11–17 for fabricating finished sutures 120 having precise cuts at both ends.

Figure 16A:
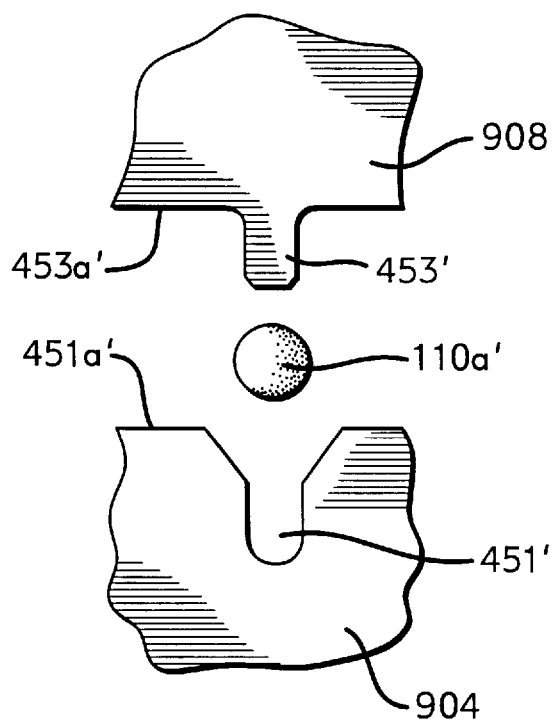
FIG. 16A is an exploded front elevational view of the opposing cutting dies 904 and 908 shown in FIG. 18.
Figure 16B:
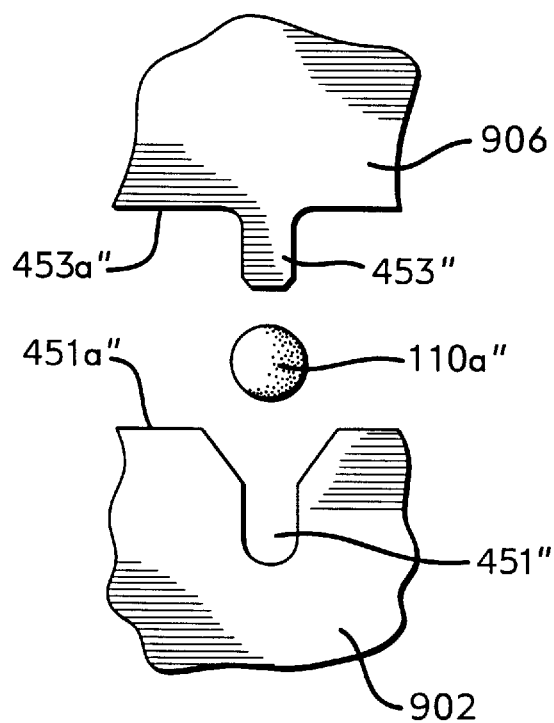
FIG. 16B is an exploded front elevational view of the opposing cutting dies 902 and 906 shown in FIG. 18.

System 900 functions substantially the same as the cutting system described in the section immediately above, except that, in system 900, the master cylinder 460 simultaneously drives a pair of cutting dies 902, 904 (respectively the first and second cutting dies) between their retracted and extended positions, the slave cylinder 462 simultaneously drives a pair of cutting dies 906, 908 (respectively the third and fourth cutting dies) between their retracted and extended positions, and the slave cylinder simultaneously moves two cutting blades 910, 912 (respectively the first and the second cutting blades) across two separate cross-sections of the thermally tipped suture material 110a. Thus, cutting dies 902, 904 are each substantially identical to cutting die 450, and cutting dies 906, 908 are each substantially identical to cutting die 452. As shown in FIG. 16A cutting dies 908 and 904 have substantially the same structure as 452 and 450 designated as second notch 453', face 453a', second channel 451', face 451a' and thermally tipped suture material 110a'. Similarly, illustrated in FIG. 16B, cutting dies 906 and 902 have substantially the same structure as 452 and 450 designated as first notch 453", face 453a", first channel 451", face 451a" and thermally tipped suture material 110a".

During operation of system 900, the master cylinder 460 first simultaneously drives the cutting dies 902, 904 from their retracted to their extended positions. As the cutting dies 902, 904 are moved to their extended positions, a separate cross-section of the thermally tipped suture material 110a suspended within station 400 is received into a groove 451 within each of the cutting dies 902, 904. Next, the slave cylinder 462 simultaneously drives the cutting dies 906, 908 from their retracted to their extended positions. After the slave cylinder 462 has driven the cutting dies 906, 908 to their extended positions, the faces 451a of the cutting dies 902, 904 stand adjacent to and abut the faces 453a of cutting dies 902, 904. After both sets of faces 451a and 453a have been brought together and the cutting dies 902, 904, 906 and 908 have "closed on" their respective cross-sections of thermally tipped suture material 110a, blades 910, 912 are simultaneously moved by slave cylinder 462 across two cross-sections of the thermally tipped suture material 110a in a direction perpendicular to the axis "x", thereby shearing the thermally tipped suture material 110a at two points adjacent to the cutting dies 906, 908 and creating two precisely cut suture ends. Following the slicing of the suture material 110a, cylinders 460 and 462 open the cutting dies 902, 904, 906 and 908 by bringing them back to their initial retracted positions.

Optical Sensor Control System

Figure 20:
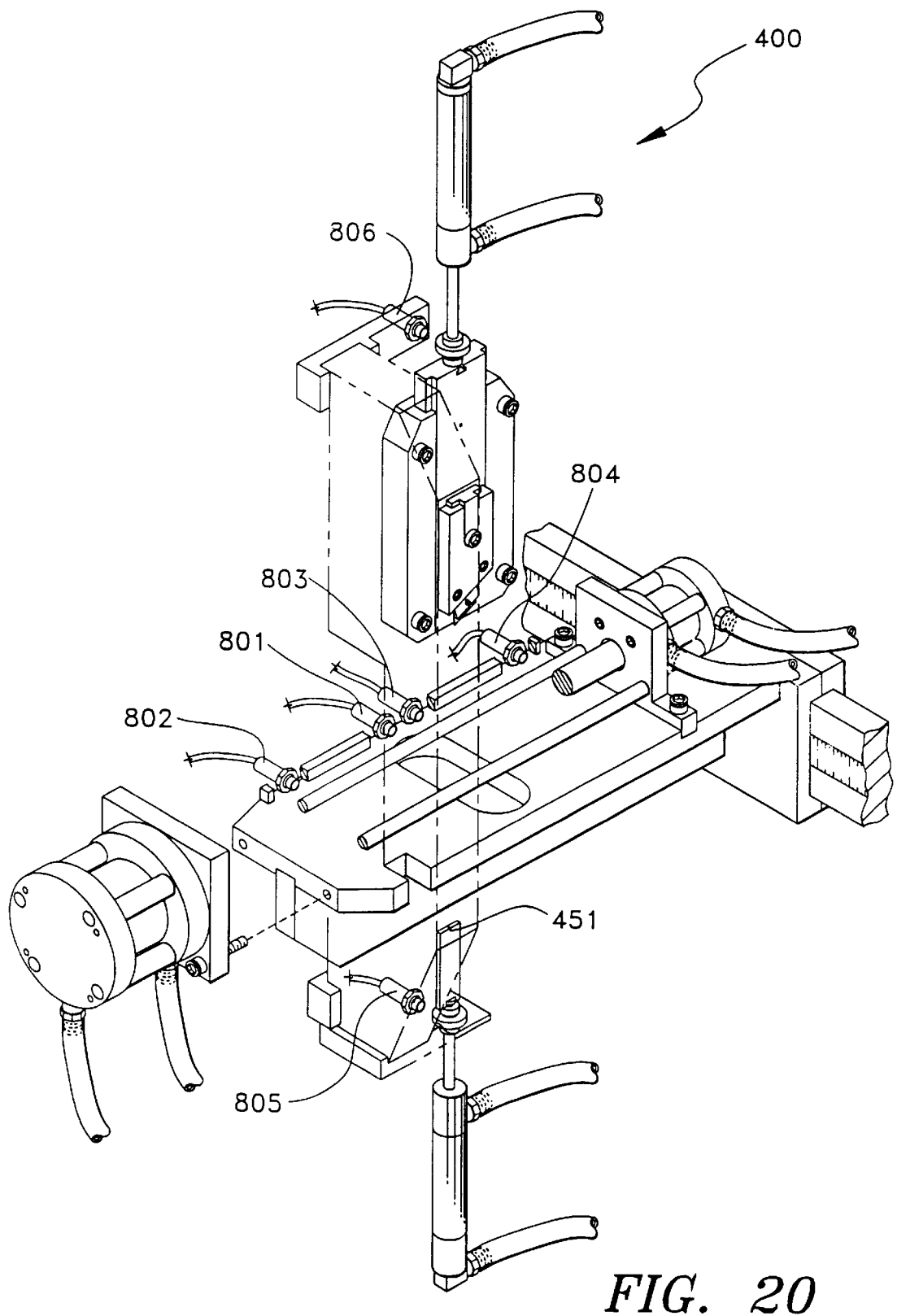
FIG. 20 shows the position of optical sensors used for monitoring the movement of the heating and cutting dies in the combined heating and cutting station shown in FIGS. 2–4 and 11–13, in accordance with a preferred embodiment of the present invention.

The open or closed state/position of the moving clamp 500, the stationary clamp 600, the heating dies 402, 404, and the cutting dies 450, 452, as well as the movement and position of the master cylinders 406, 460, the slave cylinders 408, 462, the linear actuator 550, the cutting blade 480, and the tensioning assembly 200, are monitored and controlled by a controller 800. FIG. 20 shows the positions of several optical sensors which are coupled to controller 800, and which monitor and verify the positions of the heating dies 402, 404 and cutting dies 450, 452 during the operation of the combined heating and cutting station 400. More specifically, optical sensors 801 and 802 are provided for monitoring/verifying whether heating die 404 is in its extended or retracted position; optical sensors 803 and 804 are provided for monitoring/verifying whether heating die 402 is in its extended or retracted position; optical sensor 805 is provided for monitoring/verifying whether cutting die 450 is in its extended or retracted position; and optical sensor 806 is provided for monitoring/verifying whether cutting die 452 is in its extended or retracted position. In the preferred embodiment of the present invention, controller 800 will not allow the master cylinder 406 to drive the heating die 404 to its extended position unless the sensors 805, 806 indicate that the cutting dies 450, 452 are in their retracted positions; controller 800 will not allow the slave cylinder 408 to drive the heating die 402 to its extended position unless the sensors 805, 806 indicate that the cutting dies 450, 452 are in their retracted positions and the sensors 801, 802 indicate that the heating die 404 is in its extended position; controller 800 will not allow the cylinder 460 to drive the cutting die 450 to its extended position unless the sensors 801, 802, 803 and 804 indicate that the heating dies 402, 404 are in their retracted positions; and controller 800 will not allow the cylinder 462 to drive the cutting die 452 to its extended position unless the sensors 801, 802, 803, 804 and 805 indicate that the heating dies 402, 404 are in their retracted positions and that the cutting die 450 is in its extended position.

Figure 21:
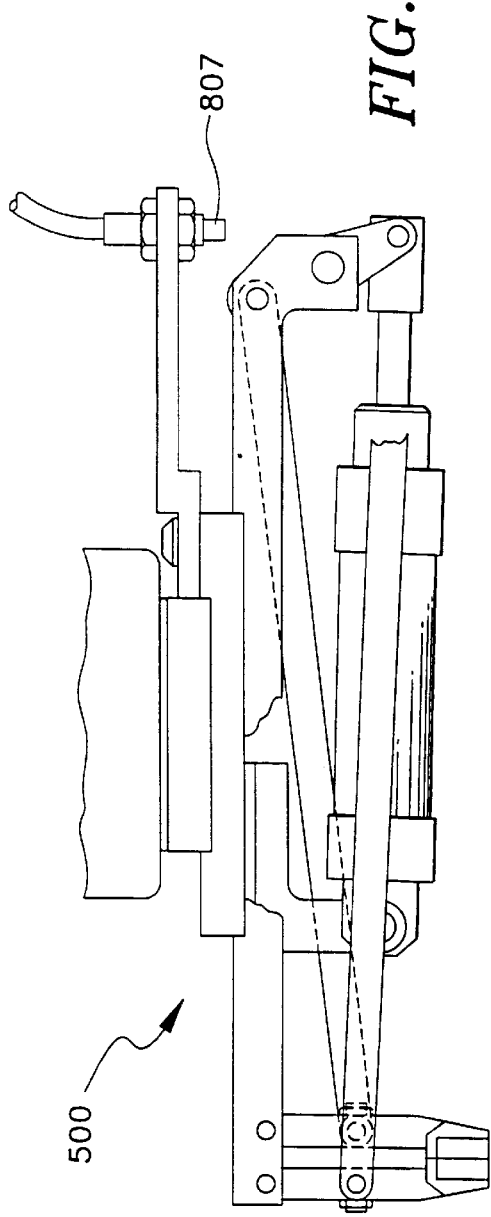
FIG. 21 is a cross-sectional view of a moving clamp shown in its closed state for grasping and advancing surgical suture material, in accordance with a preferred embodiment of the present invention.
Figure 22:
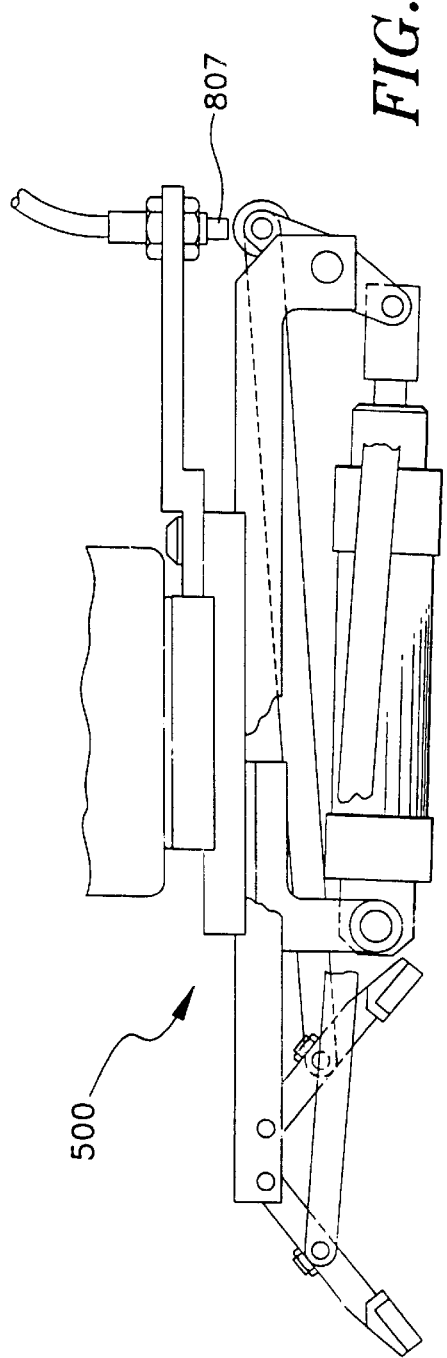
FIG. 22 is a cross-sectional view showing the moving clamp of FIG. 21 in its open state, in accordance with a preferred embodiment of the present invention.
Figure 24:
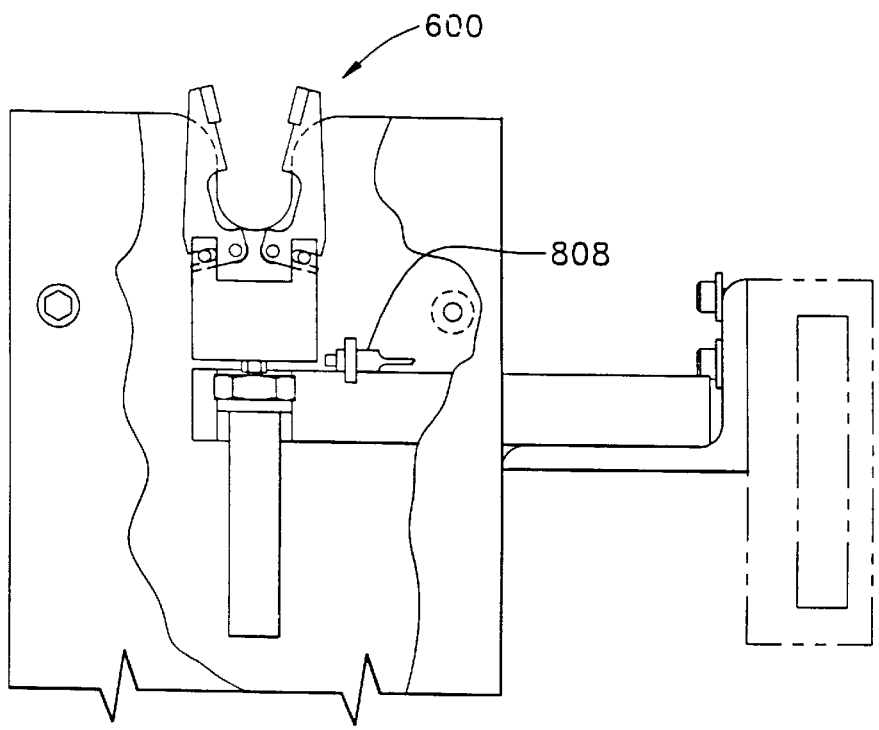
FIG. 24 is a cross-sectional view showing the stationary clamp of FIG. 23 in its open state, in accordance with a preferred embodiment of the present invention.

FIGS. 21 and 22 show the position of an optical sensor 807 which is coupled to controller 800, and which monitors and verifies the state (either open or closed) of moving clamp 500. FIGS. 23 and 24 show the position of an optical sensor 808 which is coupled to controller 800, and which monitors and verifies the state (either open or closed) of stationary clamp 600.

Suture Tensioning System

Figure 25:
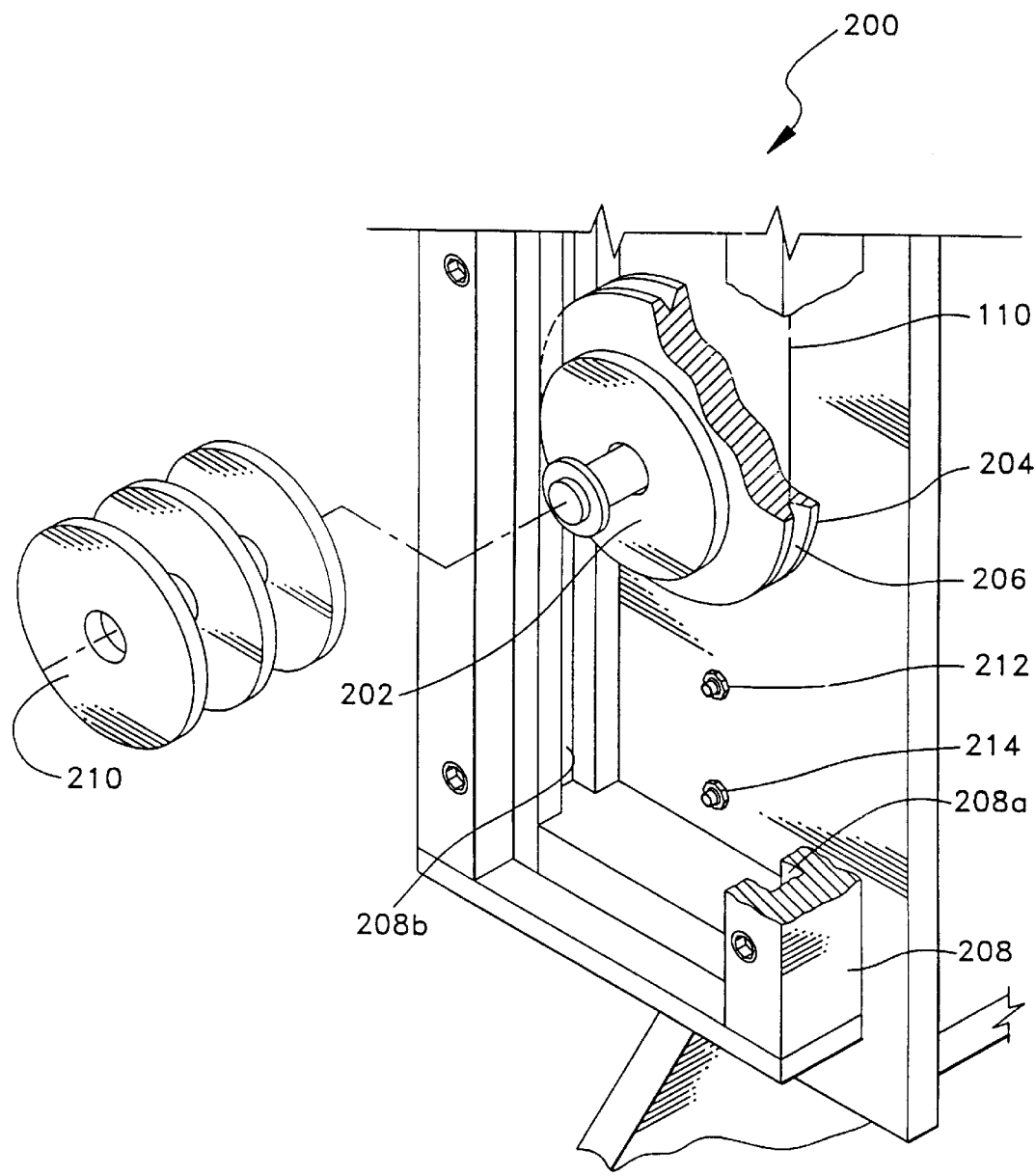
FIG. 25 is an isometric view of a system for tensioning a length of surgical suture material, in accordance with a preferred embodiment of the present invention.

Referring now to FIG. 25, there is shown an isometric view of the system 200 for tensioning a length of surgical suture material 110, in accordance with a preferred embodiment of the present invention. System 200 includes a tensioning spool 202 having a width, a weight and a circular perimeter 204 perpendicular to the width of the spool. The tensioning spool 202 has a groove 206 in its perimeter 204 for receiving the surgical suture material 110. Tensioning system 200 also includes a track 208 formed from a pair of slots 208a, 208b extending in parallel along the length of the track 208. Track 208 and slots 208a, 208b are preferably positioned along a purely vertical axis, although, in alternate embodiments (not shown), track 208 and slots 208a, 208b may be aligned along an axis that includes both horizontal and vertical components. The slots 208a, 208b function to receive and guide the tensioning spool 202 along the length of track 208 during operation of system 200. The length of the track 208 is preferably aligned perpendicularly to the width of the tensioning spool 202.

During operation of the system 200, the tensioning spool 202 is suspended vertically within slots 208a, 208b by the surgical suture material 110. While the tensioning spool 202 is suspended vertically within slots 208a, 208b by the surgical suture material 110, the weight of the tensioning spool 202 exerts a corresponding tensioning force on the suture material 110 equal to one half the weight of spool 202. In order to vary the tension exerted on the suture material 110 during operation of system 200, additional weights 210 may be added or removed from a spool arm extending from the center of spool 202.

When the moving clamp 500 described above is in its grasping state and moves from its home position 510 to its end position 512, suture material 110 suspended in the track 208 is drawn forwardly through station 400 and stationary clamp 600 of machine 10. As the suture material is drawn forwardly through the machine by the moving clamp 500, the tensioning spool 202 is pulled upwardly within track 208. However, regardless of the vertical position of the spool 202 within the track 208, the tension exerted on the suture material 110 by system 200 will be the constant and equal to one half the weight of spool 202. An optical sensor 212, coupled to controller 800, is provided for determining whether the pulling action of the moving clamp 500 has caused the spool 202 to be drawn upwardly within the track 208 past the height of the sensor 212. When optical sensor 212 detects that the tensioning spool 202 has been pulled upwardly past the location of the sensor 212, controller 800 causes a motor (not shown) coupled to the supply spool 100 to unwind unfinished surgical suture material 110 from the supply spool 100. As further unfinished surgical suture material 110 is unwound from the supply spool 100, the tensioning spool 202 moves downwardly within the track 208. In the preferred embodiment, controller 800 continues to unwind unfinished surgical suture material 110 from the supply spool 100 until the tensioning spool 202 falls below the level of optical sensor 212.

An optical sensor 214 is provided at the bottom of track 208 for determining whether there has been a break in the surgical suture material 110 or a loss of tension in the suture material within machine 10. Since, during normal operation, the tensioning spool 202 should not fall below the level of optical sensor 212, a break in suture material 110 or a loss of suture tension within machine 10 will be signaled by sensor 214 if the sensor determines that the tensioning spool 202 has fallen to the level of the sensor 214.

Although tensioning system 200 has been described in connection with the tensioning of surgical suture material, it will be understood by those skilled in the art that tensioning system 200 may be used for tensioning any type of string or yarn.

Knot Detection System

Referring now to FIGS. 26 and 27, there are shown two isometric views of an optical detection system 300 for detecting knots in surgical suture material 110 passing through system 300, in accordance with a preferred embodiment of the present invention. Knot detector system 300 includes an optical light source 302 for directing a plane of light 304 at an optical light detector 306 when surgical suture material 110 is positioned between the optical light source 302 and the optical light detector 306 (shown in FIG. 28). The optical light source 302 is preferably formed of a plurality of optical fibers 302a having their terminating ends aligned along the optical plane 304. Controller 800 is coupled to an output of the optical light detector 306 for processing the signals output by detector 306 and determining whether a knot exists in the suture material 110 positioned between the light source 302 and light detector 306. More particularly, by comparing a magnitude of a shadow 308 cast on the optical light detector 306 by the suture material 110 against a predetermined threshold, controller 800 determines whether or not a knot exists in the suture material 110 positioned between the light source 302 and light detector 306. In a preferred embodiment, the predetermined threshold used in this comparison corresponds to a magnitude of a shadow 308a cast on the optical light detector 306 by an unknoted cross-section of suture material 110. In a still further preferred embodiment, controller 800 will determine that a knot exists in the suture material 110 passing through system 300 only if the magnitude of the shadow cast on light detector 306 by suture material 110 exceeds by at least 30% the magnitude of a shadow 308a cast on the optical light detector 306 by an unknoted cross-section of suture material 110.

Although knot detection system 300 has been described in connection with the detection of knots in surgical suture material, it will be understood by those skilled in the art that knot detection system 300 may be used for detecting knots in any type of string or yarn.

Extended Length Suture Mode

Figure 29:
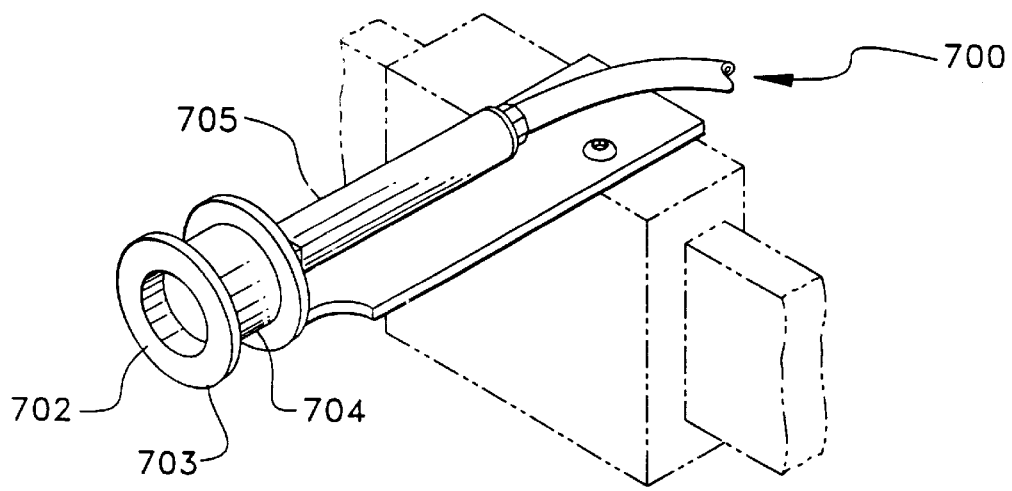
FIG. 29 is an isometric view of a suture material holding arm which is used for producing sutures having lengths that exceed the length of the machine of FIG. 1, in accordance with a preferred embodiment of the present invention.
Figure 30:
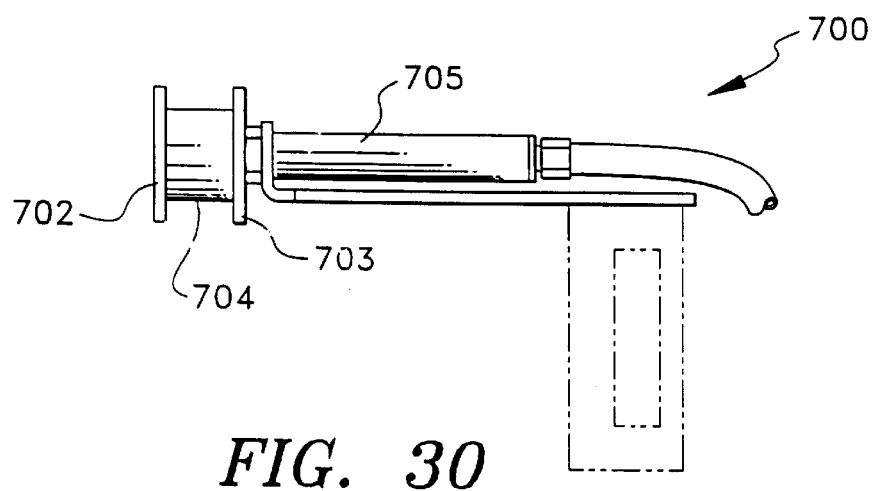
FIG. 30 is a cross-sectional view showing the suture material holding arm of FIG. 29 in its retracted position.
Figure 31:
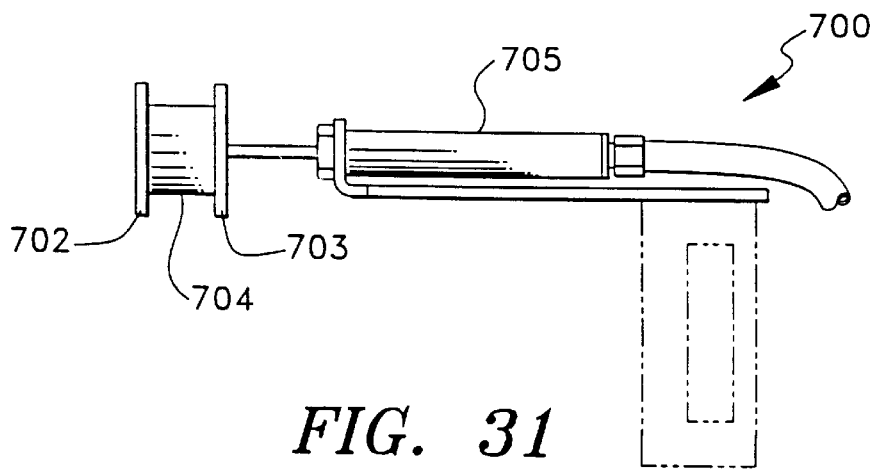
FIG. 31 is a cross-sectional view showing the suture material holding arm of FIG. 29 in its extended position.

Although, in the process described above, machine 10 was used to manufacture a finished surgical suture 120 having a length that was less than length of the linear actuator 550, machine 10 may also be used in an extended length suture mode, described below, in order to make finished surgical sutures which are longer than linear actuator 550. As shown in FIG. 1, and also in FIGS. 29–31, a suture material holding arm 700 affixed to machine 10 is provided for holding suture material during the manufacture of extended length surgical sutures. Suture material holding arm 700 includes an end portion 704 formed of a cylindrical central portion bounded by sides 702, 703. An actuator 705, coupled to controller 800, drives the end portion 704 between its retracted position (shown in FIGS. 29–30) and its extended position (shown in FIG. 31). When machine 10 functions in its extended length suture mode, actuator 705 maintains end portion 704 in its extended position; otherwise, actuator 705 maintains end portion 704 in its retracted position.

During operation of the machine 10 in the extended length suture mode, the moving clamp 500 initially grasps or closes on the unfinished surgical suture material 110 at the home position 510. Next, while the moving clamp 500 remains in its grasping or closed state, the linear actuator 550 drives the moving clamp 500 from its home position 510 to the end position 512. As the linear actuator 550 drives moving clamp 500 from its home position 510 to its position 512, the moving clamp 500 pulls a length of the unfinished surgical suture material 110 through the combined heating and cutting station 400 and through the stationary clamp 600. After the moving clamp reaches its end position 512, the stationary clamp 600 grasps or closes on the unfinished surgical suture material 110 positioned within the stationary clamp 600. The moving clamp 500 then releases the unfinished surgical suture material 110 in its grasp, allowing the suture material 110 previously grasped by the moving clamp 500 to fall onto and be held by the end portion 704. Next, while the moving clamp is in its open or nongrasping state, the linear actuator 550 drives the moving clamp 500 from its end position 512 to its home position 510, where the moving clamp 500 again grasps or closes on the unfinished surgical suture material 110 at the home position 510. After the moving clamp 500 grasps the unfinished surgical suture material 110 at the home position 510 for the second time, the stationary clamp 600 opens. Thereafter, while the moving clamp 500 remains in its grasping or closed state and the stationary clamp 600 remains in its open state, the linear actuator 550 again drives the moving clamp 500 from its home position 510 to the end position 512. After the moving clamp 500 reaches its end position 512 for the second time, the stationary clamp 600 again grasps or closes on the unfinished surgical suture material 110 positioned within the stationary clamp 600.

After the unfinished surgical suture material 110 has been "pulled twice" by the moving clamp 500 as described in the paragraph above, the heating dies 402, 404 and the cutting dies 450, 452 in the combined heating and cutting station 400 function as described above to thermally form and cut a length of surgical suture tip material positioned within the station. After the cutting dies 450, 452 move from their closed position to their open position following the cutting of the suture tip, the stationary clamp 600 releases the surgical suture material within its grasp. As the stationary clamp opens and releases the previously grasped surgical suture material, a finished surgical suture 120 having a thermally formed and cut tip falls by gravity onto an arm affixed to the stationary clamp 600. Since the moving clamp 500 pulled the suture material 110 two times consecutively before the combined heating and cutting station 400 thermally formed and cut the suture tip, the resulting finished surgical suture 120 produced by the extended length suture mode may have a length which is greater than the length of the linear actuator 550.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. An apparatus for cutting a surgical suture at first and second different locations along a length of said surgical suture said apparatus comprising:

(A) a first cutting die having a first face with a first channel for receiving at least a first portion of a cross-section of said surgical suture;

(B) a second cutting die having a second face with a second channel for receiving at least a second portion of said cross-section of said surgical suture;

(C) a third cutting die having a third face;

(D) a fourth cutting die having a fourth face;

(E) a first cutting blade for cutting said surgical suture adjacent to said first face when said first face of said first cutting die is positioned against said third face of said third cutting die; and (F) a second cutting blade for cutting said surgical suture adjacent to said second face when said second face of said second cutting die is positioned against said fourth face of said fourth cutting die wherein the first cutting blade is positioned at the first location and the second cutting blade is position at the second location along the length of the surgical suture.

2. The apparatus of claim 1, wherein said first channel and second channel are aligned along a common axis, and said first cutting blade and second cutting blade are positioned to cut said surgical suture in a direction perpendicular to said common axis.

3. The apparatus of claim 1, further comprising:

(G) a mechanical actuator for moving said first face of said first cutting die against said third face of said third cutting die and for moving said second face of said second cutting die against said fourth face of said fourth cutting die.

4. The apparatus of claim 3, wherein said mechanical actuator is positioned to simultaneously move said first face of said first cutting die against said third face of said third cutting die while said mechanical actuator moves said second face of said second cutting die against said fourth face of said fourth cutting die.

5. The apparatus of claim 4, wherein said first face of said first cutting die and said third face of said third cutting die define a first singular cutting die opening when said first face of said first cutting die is positioned against said third face of said third cutting die, and wherein said second face of said second cutting die and said fourth face of said fourth cutting die define a second singular cutting die opening when said second face of said second cutting die is positioned against said fourth face of said fourth cutting die, said first and second singular cutting die openings being aligned along said common axis.

6. The apparatus of claim 5, wherein said first singular cutting die opening has a cross-section perpendicular to said common axis that is adapted to compress said cross-section of said surgical suture at a first location along said length of said surgical suture when said first face of said first cutting die is positioned against said third face of said third cutting die, and wherein said second singular cutting die opening has a cross-section perpendicular to said common axis that is adapted to compress said cross-section of said surgical suture at a second location along said length of said surgical suture when said second face of said second cutting die is positioned against said fourth face of said fourth cutting die.

7. The apparatus of claim 6, wherein said first channel in said first face of said first cutting die is sized to contain all of said cross-section of said surgical suture at said first location along said length of said surgical suture, and wherein second channel in said second face of said second cutting die is sized to contain all of said cross-section of said surgical suture at said second location along said length of said surgical suture.

8. The apparatus of claim 7, wherein said cross-section of said surgical suture at said first location is circular, and wherein said cross-section of said surgical suture at said second location is circular.

9. The apparatus of claim 8, wherein said first channel in said first face has a cross-section that is semi-circular in shape, and wherein said second channel in said second face has a cross-section that is semi-circular in shape.

10. The apparatus of claim 9, wherein said third face of said third cutting die includes a first notch having a rectangular shape, said first channel in said first face and said first notch in said third face defining said first singular cutting die opening when said first face of said first cutting die is positioned against said third face of said third cutting die, and wherein said fourth face of said fourth cutting die includes a second notch having a rectangular shape, said second channel in said second face and said second notch in said fourth face defining said second singular cutting die opening when said second face of said second cutting die is positioned against said fourth face of said fourth cutting die.

11. The apparatus of claim 10, further comprising:

(I) a controller, coupled to said mechanical actuator, for signaling said at least one mechanical actuator to retract said first cutting die, second cutting die, third cutting die and fourth cutting die after said first cutting blade and second cutting blade have cut said surgical suture.

12. The apparatus of claim 11, wherein said mechanical actuator comprises a master cylinder coupled to said first cutting die and second cutting die for moving said first cutting die and second cutting die from a retracted position to an extended position with a first force, and a slave cylinder coupled to said third cutting die and fourth cutting die for moving said third cutting die and fourth cutting die from a retracted position to an extended position positions with a second force that is smaller than said first force.

* * * * *